United States Patent
Wolfrum et al.

(10) Patent No.: US 9,777,036 B2
(45) Date of Patent: Oct. 3, 2017

(54) ROR GAMMA MODULATORS

(71) Applicant: ETH ZÜRICH, ETH TRANSFER, Zürich (CH)

(72) Inventors: Christian Wolfrum, Weiningen (CH); Erick Carreira, Zumikon (CH); Bettina Meissburger, Eppelheim (DE)

(73) Assignee: ETH Zürich, Zürich (CH)

( * ) Notice: Subject to any disclaimer, the term of this patent is extended or adjusted under 35 U.S.C. 154(b) by 12 days.

(21) Appl. No.: 14/345,597

(22) PCT Filed: Sep. 18, 2012

(86) PCT No.: PCT/EP2012/068332
§ 371 (c)(1),
(2) Date: Mar. 18, 2014

(87) PCT Pub. No.: WO2013/041519
PCT Pub. Date: Mar. 28, 2013

(65) Prior Publication Data
US 2014/0343023 A1 Nov. 20, 2014

(30) Foreign Application Priority Data
Sep. 19, 2011 (EP) .................... 11007610

(51) Int. Cl.
- *C07J 9/00* (2006.01)
- *A61K 31/575* (2006.01)
- *A61K 31/58* (2006.01)
- *C07J 71/00* (2006.01)

(52) U.S. Cl.
CPC ............ *C07J 9/005* (2013.01); *A61K 31/575* (2013.01); *A61K 31/58* (2013.01); *C07J 71/001* (2013.01)

(58) Field of Classification Search
CPC ....... A61K 31/575; A61K 31/58; C07J 9/005; C07J 71/001
See application file for complete search history.

(56) References Cited

U.S. PATENT DOCUMENTS 9,243,027 B2   1/2016  Pellicciari

FOREIGN PATENT DOCUMENTS

| JP | H07-126283 A | 5/1995 |
|---|---|---|
| JP | 2000-26300 | 1/2000 |
| JP | 2004-510682 | 4/2004 |
| JP | 2005-533807 | 11/2005 |
| JP | 2011-511752 A | 4/2011 |
| WO | WO 96/40728 | 12/1996 |
| WO | WO 97/36579 | 10/1997 |
| WO | WO 00/57915 | 10/2000 |
| WO | WO 01/21577 A2 | 3/2001 |
| WO | WO 01/68609 A1 | 9/2001 |
| WO | WO 01/96302 A1 | 12/2001 |
| WO | WO 02/051232 A2 | 7/2002 |
| WO | WO 02/051838 A1 | 7/2002 |
| WO | WO 04/000869 A1 | 12/2003 |
| WO | WO 2006/116814 A1 | 9/2006 |
| WO | WO 2009/105897 A1 | 9/2009 |
| WO | WO 2011/022838 | 3/2011 |

OTHER PUBLICATIONS

Kim, S.K. et al., "Diabetes Correction in Pancreatectomized Canines by Orally Absorbable Insulin-Deoxycholate Complex," Molecular Pharmaceutics, 2010, vol. 7, No. 3, pp. 708-717, XP008157487.

Raskovic, A. et al., "Joint Effect of Commercial Preparations of Stevia rebaudiana Bertoni and Sodium Monoketocholate on Glycemia in Mice," European Journal of Drug Metabolism and Pharmacokinetics, 2004, vol. 29, No. 2, pp. 83-86, XP008157533.

Kurosawa T. et al., "Capillary Gas Chromatographic Determination of C27-bile Acids in Biological Samples and Its Applicaiton to the Urine of a Patient with Zellweger Syndrome," Analytical Sciences, Dec. 1996, vol. 12, No. 6, pp. 839-846, XP008157531.

André, E. et al, "A novel isoform of the orphan nuclear receptor RORβ is specifically expressed in pineal gland and retina", Gene, 1998, v. 216, pp. 277-283.

Batterham, R.L. et al., "Pancreatic polypeptide reduces appetite and food intake in humans", Jnl of Clin. Endocrinology & Metab., 2003, v. 88(8), pp. 3989-3992.

(Continued)

Primary Examiner — Barbara P Badio
(74) Attorney, Agent, or Firm — Pauley Erickson & Kottis

(57) ABSTRACT

The present invention relates to compounds of formula I, or a pharmaceutically acceptable salt thereof,

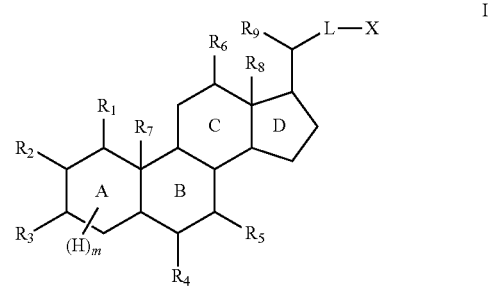

for use in the treatment or prevention, suppression or amelioration of a disease mediated by the ROR gamma receptor in a subject in need thereof, in particular diabetes and diabetes-related disorders, specifically type II diabetes, methods of their production, as well as methods of treatment or prevention of such diseases.

19 Claims, 5 Drawing Sheets

(56) References Cited

OTHER PUBLICATIONS

Becker-André, M., et al., "Identification of Nuclear Receptor mRNAs by RT-PCR Amplification of Conserved Zinc-Finger Motif Sequences", Biochem. & Biophys. Research Comm., Aug. 16, 1993, vol. 194 No. 3, pp. 1371-1379.
Fleming, I. et al., "The Phenyldimethylsilyl Group as a Masked Hydroxy Group", J. Chem. Soc. Perkin Trans., 1995, vol. 1, pp. 317-337.
He, Y-W et al., "RORγt, a Novel Isoform of an Orphan Receptor, Negatively Regulates Fas Ligand Expression and IL-2 Production in T Cells", Immunity, Dec. 1998, v. 9, pp. 797-806.
Kieć-Kononowicz, K. et al., "Importance of the lipophilic group in carbamates having histamine H3-receptor antagonist activity", Pharmazie, 2000, v. 55 (5), pp. 349-355.
Laiewska, D. et al., "Piperidine-containing histamine H3-receptor antagonists of the carbamate series: variation of the spacer length", Pharmazie, 2001, v. 56(12), pp. 937-932.
Litvak, D.A. et al., "Characterization of Two Novel Proabsorptive Peptide YY Analogs, BIM-43073D and BIM-43004C", Dig.Diseases & Sciences, Mar. 1999, v. 44(3), pp. 643-648.
Mangelsdorf, D.J. et al., "The Nuclear Receptor Superfamily: The Second Decade", Cell, Dec. 15, 1995, v. 83, pp. 835-839.
Opsenica, D. et al., "Cholic Acid Derivatives as 1,2,4,5-Tetraoxane Carriers: Structure and Antimalarial and Antiproliferative Activity", J. Med. Chem., 2000, v. 43, pp. 3274-3282.
Reidemeister, S. et al., "Substituted N-phenylcarbamates as histamine H3 receptor antagonists with improved in vivo potency", Pharmazie, 2000, v. 55(2), pp. 83-86.
Rohacova, J. et al., "Synthesis of new, UV-photoactive dansyl derivatives for flow cytometric studies on bile acid uptake", Organic & Biomolecular Chemistry, 2009, v. 7, pp. 74973-74980.
Sasse, A. et al., "New Histamine H3-Receptor Ligands of the Proxifan Series: Imoproxifan and Other Selective Antagonists with High Oral in Vivo Potency", J. Med.Chem., 2000, v. 43, pp. 3335-3343.
Sasse, A. et al, "Benzophenone Derivatives and Related Compounds as Potent Histamine H3-Receptor Antagonists and Potential PET/SPECT Ligands", Arch. Pharm. Med. Chem., 2001, v. 334, pp. 45-52.
Tohma, M. et al., "Synthesis of the 1β-Hydroxylated Bile Acids, Unusual Bile Acids in Human Biological Fluids", Chem. Pharm. Bull., 1986, v. 34, pp. 2890-2899.
Japanese Patent Office (JPO), Final Rejection, Japanese Patent Application No. 2014-530269, mailed Mar. 28, 2017—English Translation Only (3 pages).
Japanese Patent Office (JPO), Office Action "Notice of Reasons for Rejection," Japanese Patent Applicaiton No. P2014-530269, mailed Jun. 21, 2016, English I ranslatlon only (6 pages).
Clayton, P.T., et al., "The bile acid composition of gastric contents from neonates with high intestinal obstruction," Biochem. J., 1982, vol. 206, pp. 489-498.
Tohma, M., et al., "Syntheses of the 1β-Hydroxylated bile acids and identification of 1β,3α.7α-Trihydroxy- and 1β,3α,7α-Tetrahydroxy-5β-Cholan-24-OIC Acids in human Meconium," Chem. Pharm. Bull., 1985, vol. 33, pp. 3071-3073.
Mahara, R., et al., "Determination of 1β-Hydroxylated Bile Acids and Related Compounds in Human Biological Fluids by Gas chromatography-Mass Spectrometry," Analytical Sciences, 1987, vol. 3, pp. 449-452.
Shoda, J., et al., "Similarity of unusual bile acids in human umbilical cord blood and amniotic fluid from newborns and in sera and urine from adult patients with cholestatic liver diseases," J. Lipid Research, 1988, vol. 29, pp. 847-858.
Setchell, K., et al., "Hepatic Bile Acid Metabolism during Early Development Revealed from the Analysis of Human Fetal Gallbladder Bile, " J. Biol., Chem., 1988 vol. 263, pp. 16637-16644.
Ikegawa, S., et al., "Conjugated 1β-Hydroxycholic Acid in the Urine of Newborns and Pregnant Women Measured by Radioimmunoassay Using Antisera Raised against N-(1β-Hydroxycholyl)-2-aminopropionic Acid-Bovine Serum Albumin Conjugate," Chem. Pharm. Bull., 1992, vol. 40, pp. 1835-1838.
Yamaguchi, K., et al., "Measurement of Transport Activities of Bile Acids in Human Multidrug Resistance-Associated protein 3 Using Liquid Chromatography—Tandem Mass Spectrometry," Analytical Sciences, 2010, vol. 26, pp. 317-323.
Strandvik, B., et al., "Tetrahydroxylated bile acids in healthy human newborns," Eur. J. Clin. Invest., 1982, vol. 12, pp. 301-305.
Yang, Y., et al., "Analysis of Bile Acids and Bile Alcohols in Urine by Capillary Column Liquid Chromatography-Mass Spectrometry using Fast Atom Bombardment or Electrospray ionization and Collision-induced Dissociation," Biomedical Chromatography, 1997, vol. 11, pp. 240-255.
Bremmelgaard, A., et al., "Hydroxylation of bile acids in man," Falk Symposium, 1981, vol. 29, pp. 103-109.
Back, P., et al., "Developmental Pattern of Bile Acid Metabolism as Revealed by Bile Acid Analysis of Meconium," Gastroenterology, 1980, vol. 78, pp. 671-676.

ROR GAMMA MODULATORS

BACKGROUND OF THE INVENTION

Field of the Invention

The present invention relates to compounds for use in the treatment or prevention, suppression or amelioration of a disease mediated by the ROR gamma receptor in a subject in need thereof, in particular diabetes and diabetes-related disorders, specifically type II diabetes, methods of production of such compounds, as well as methods of treatment or prevention of such diseases.

Discussion of Related Art

Worldwide, there are about 250 million people that suffer from diabetes (type I and type II) and the number is projected to double in next two decades. Type 1 diabetes is based on lack of insulin production by the pancreas. Although the causes are not entirely known, type 1 diabetes is a multi-factorial autoimmune disease that results from the specific and progressive destruction of insulin producing beta-cells in the pancreas. Typical treatment of type 1 diabetes includes (multiple) administration of insulin, which however does not cure diabetes or prevent its eventual effects such as kidney failure, blindness, nerve damage, amputations, heart attack and stroke. Even with insulin treatment, type 1 diabetes usually results in a drastic reduction in quality of life and shortens the average life span by 15 years. Type 2 diabetes, also called non-insulin dependent diabetes mellitus, is a heterogeneous disease characterized by abnormalities in carbohydrate and fat metabolism. The causes of type 2 diabetes are multi-factorial and include both genetic and environmental elements that affect beta-cell function and insulin sensitivity in tissues such as muscle, liver, pancreas and adipose tissue. As a consequence impaired insulin secretion is observed and paralleled by a progressive decline in beta-cell function and chronic insulin resistance. The inability of the endocrine pancreas to compensate for peripheral insulin resistance leads to hyperglycaemia and onset of clinical type 2 diabetes characterized by hyperglycemia, insulin resistance, absolute or relative insulin deficiency, hyperglucagonemia, and increased hepatic glucose production. However, there is still no definitive treatment for the disease.

Applicants have now surprisingly found that the retinoid-receptor related orphan receptors (ROR) may act as a central regulator of adipogenesis. The retinoid-receptor related orphan receptors consist of three family members, namely ROR alpha (Becker-Andree, Biochem. Biophys. Res. Commun. 1993, 194:1371), ROR beta (Andre et al., Gene 1998, 516:277) and ROR gamma (He et al, Immunity 1998, 9:797) and constitute the NR1F (ROR/RZR) subgroup of the nuclear receptor superfamily (Mangelsdorf et al., Cell 1995, 83:835). Applicants have shown that in particular the ROR gamma receptor, which has been linked exclusively to immunological functions, may inhibit adipogenesis and may allow protection from diet or genetically induced insulin resistance.

Thus the present invention provides compounds of the invention, in particular compounds based on a polyhydroxylated cholane skeleton, that are able to act as ROR (gamma) receptor modulators or ligands, thereby influencing the biological pathways in adipogenesis controlled by ROR (gamma), and thus may be useful for the prevention, treatment and amelioration of diabetes and diabetes-related disorders, in particular type II diabetes.

SUMMARY OF THE INVENTION

The present invention relates in a first aspect to compounds based on a polyhydroxylated cholane skeleton and pharmaceutically acceptable salts or stereoisomers thereof for use as modulators of the ROR receptor, in particular, as selective ROR gamma receptor ligands (also hereinafter called compounds of the invention or ROR gamma receptor ligands or modulators of the present invention) having the general formula I

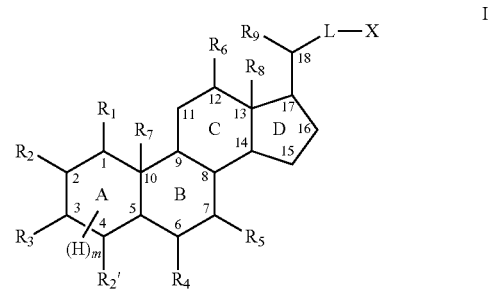

wherein $R_1$, $R_2$, $R_{2'}$ are independently of each other H, hal, —$OR_a$, —$SR_a$, —$NR_aR_b$, —$COOR_a$, —$CONR_aR_b$, wherein $R_a$ and $R_b$ are independently of each other H or (C1-6)alkyl, or $R_1$, $R_2$ form together with the C-atoms to which they are linked an epoxy group;

$R_3$, $R_4$, $R_5$, $R_6$, are independently of each other H, hal, —$OR_a$, —$SR_a$, —$NR_aR_b$, —$COOR_a$, —$CONR_aR_b$, oxo, thio wherein $R_a$ and $R_b$ are independently of each other H or (C1-6)alkyl;

$R_7$, $R_8$, $R_9$ are independently of each other H, (C1-10) alkyl, wherein one or more non neighbouring $CH_2$ groups may be replaced with —O—, —S—, —CO—, —CO—O—, —O—CO—, —$NR_a$—, —CO—$NR_a$—, —$NR_a$—CO—, —C=C—, or —C≡C—; wherein $R_a$ is FT or (C1-6)alkyl;

L is a linking group, such as straight-chain or branched C(1-12)alkyl, which is unsubstituted or substituted by at least one CN, hal, OFT, $NR_aR_b$, $COOR_a$, $NO_2$, and wherein one or more of the non-adjacent $CH_2$ groups may independently be replaced by a group selected from —O—, —CO—, —CO—O—, —O—CO—, —$NR_a$—, —$NR_a$—CO—, —CO—$NR_a$—, —CH=CH—, —C≡C—, wherein $R_a$ and $R_b$ are independently of each other H or C(1-6)alkyl, X is H, —$OR_a$, —$SR_a$, —$NR_aR_b$, —$COOR_c$, —$CONR_aR_c$; wherein $R_a$ and $R_b$ are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl;

m is 0 to 5.

In specific embodiments, the compounds of the invention are based on a polyhydroxylated cholane skeleton having a -L-X— substituent at C17, and wherein the hydroxyl (or oxo-) substituents are preferably in one or more positions selected from C1, C3, C6, C7, C12, more preferably wherein the hydroxyl (or oxo-) substituents are at a total of three or four positions selected from C1, C3, C6, C7, C12, most preferably wherein the hydroxyl (or oxo-) substituents are at a total of three or four positions selected from C1, C3, C6, C7, C12 of which one hydroxyl (or oxo-substituent) is in position C1 or C6.

Preferred compounds of the invention have three hydroxyl (or oxo-substituents) at positions C1, C3 and C7; C1, C3 and C12; C1, C7 and C12; C3, C6 and C7; C3, C6 and C12; C6, C7 and C12; C1, C3 and C6; C1, C6 and C7; and C1, C6, and C12.

Other preferred compounds of the invention have four hydroxyl (or oxo-substituents) at positions C1, C3, C7 and C12; C3, C6, C7 and C12; C1, C3, C6 and C7; C1, C3, C6 and C12; and C1, C6, C7 and C12.

In some embodiments, the invention includes compounds of formula II and pharmaceutically acceptable salts or stereoisomers thereof, preferably its stereoisomeric form IIa,

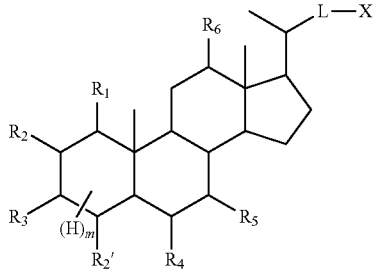

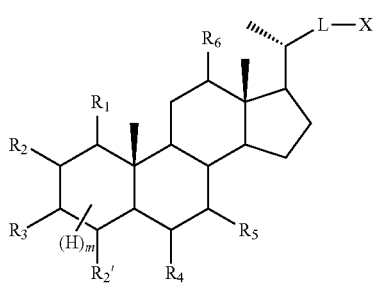

wherein $R_1$, $R_2$ are independently of each other H, hal, —$OR_a$, —$SR_a$, —$NR_aR_b$, $COOR_a$, —$CONR_aR_b$, wherein $R_a$ and $R_b$ are independently of each other H or (C1-6)alkyl, or $R_1$, $R_2$ form together with the C-atoms to which they are linked an epoxy group;

$R_3$, $R_4$, $R_5$, $R_6$, are independently of each other H, hal, —$OR_a$, —$SR_a$, —$NR_aR_b$, —$COOR_a$, —$CONR_aR_b$, oxo, thio wherein $R_a$ and $R_b$ are independently of each other H or (C1-6)alkyl;

$R_{2'}$ is H or hal,

L is a linking group, such as straight-chain or branched C(1-12)alkyl, which is unsubstituted or substituted by at least one CN, hal, OH, $NR_aR_b$, $COOR_a$, $NO_2$, and wherein one or more of the non-adjacent $CH_2$ groups may independently be replaced by a group selected from —O—, —CO—, —CO—O—, —O—CO—, —$NR_a$—, —$NR_a$—CO—, —CO—$NR_a$—, —CH=CH—, —C≡C—; wherein $R_a$ and $R_b$ are independently of each other H or C(1-6)alkyl, X is H, —$OR_a$, —$SR_a$, —$NR_aR_b$, —$COOR_c$, —$CONR_aR_c$; wherein $R_a$ and $R_b$ are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl;

m is 0 to 5.

In one preferred embodiment, at least three, preferably three or four, groups selected from $R_1$, $R_3$, $R_4$, $R_5$ and $R_6$ are —$OR_a$ or oxo, wherein $R_a$ is H or C(1-6)alkyl.

In another preferred embodiment, $R_1$ and/or $R_4$ are —$OR_a$ or oxo.

More specifically, the compounds of the invention are characterized by formula I, II or IIa, wherein either (i) $R_4$ and $R_6$ are —$OR_a$, or (ii) $R_1$ and $R_6$ are —$OR_a$, or (iii) $R_3$ is either —$OR_a$ or oxo and $R_6$ is —$OR_a$, or (iv) $R_5$ and $R_6$ are —OR, and the remaining groups in each of the compounds have the following meaning (where applicable):

$R_1$ is H, hal, —$OR_a$, —$SR_a$, —$NR_aR_b$, —$COOR_a$, —$CONR_aR_b$, preferably H, —$OR_a$, —$NR_aR_b$, wherein $R_a$ and $R_b$ are independently of each other H or (C1-6)alkyl, or $R_1$ forms together with $R_2$ and the C-atoms to which $R_1$, $R_2$ are linked to an epoxy group;

$R_2$ is H, hal, —$OR_a$, —$SR_a$, —$NR_aR_b$, —$COOR_a$, —$CONR_aR_b$, preferably H or hal, wherein $R_a$ and $R_b$ are independently of each other H or (C1-6)alkyl, or $R_2$ forms together with $R_1$ and the C-atoms to which $R_1$, $R_2$ are linked to an epoxy group;

$R_3$, $R_4$, $R_5$ are independently of each other H, hal, —$OR_a$, —$SR_a$, —$NR_aR_b$, —$COOR_a$, —$CONR_aR_b$, oxo, thio, preferably H, oxo, —$OR_a$, —$NR_aR_b$, wherein $R_a$ and $R_b$ are independently of each other H or (C1-6)alkyl;

$R_{2'}$ is H or hal,

L is a straight-chain or branched C(1-12)alkyl, which is unsubstituted and wherein one or more of the non-adjacent $CH_2$ groups may independently be replaced by a group selected from —O—, —CO—, —CO—O—;

X is H, —$OR_a$, —$SR_a$, —$NR_aR_b$, —$COOR_c$, —$CONR_aR_c$; wherein $R_a$ and $R_b$ are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl;

m is 0 to 5.

In preferred embodiments the invention includes compounds of formula IV and V (with $R_3$ being —$OR_a$ or oxo) and pharmaceutically acceptable salts or stereoisomers thereof,

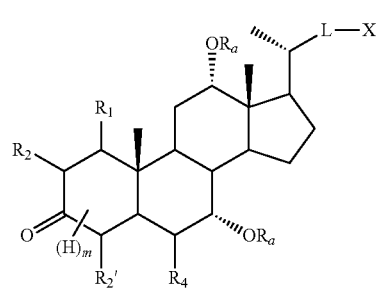

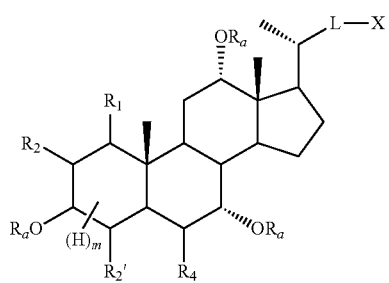

wherein $R_1$ is H, hal, —$OR_a$, —$SR_a$, —$NR_aR_b$, —$COOR_a$, —$CONR_aR_b$, preferably H, —$OR_a$, —$NR_aR_b$, wherein $R_a$ and $R_b$ are independently of each other H or (C1-6)alkyl, or $R_1$ forms together with $R_2$ and the C-atoms to which $R_1$, $R_2$ are linked to an epoxy group;

R$_2$ is H or hal, or R$_2$ forms together with R$_1$ and the C-atoms to which R$_1$, R$_2$ are linked to an epoxy group;

R$_{2'}$ is H or hal,

R$_4$ is H, hal, —OR$_a$, —SR$_a$, —NR$_a$R$_b$, —COOR$_a$, —CONR$_a$R$_b$, oxo, thio, preferably H, oxo, —OR$_a$, —NR$_a$R$_b$, wherein R$_a$ and R$_b$ are independently of each other H or (C1-6)alkyl, L is a straight-chain or branched C(1-2)alkyl;

X is H, —OR$_a$, —COOR$_c$, —CONR$_a$R$_c$, wherein R$_a$ is H or (C1-6)alkyl and R$_c$ is —H, —(C1-6)alkyl, —NH—(CH$_2$)$_n$—CO$_2$R$_a$ or —NH—(CH$_2$)$_p$—SO$_3$R$_a$, wherein n, p is 1, 2, or 3 and R$_a$ is —H or —(C1-6)alkyl, R$_a$ is H or C(1-6)alkyl, and m is 0 to 5.

In a further aspect, the methods of invention also relates to convenient and efficient methods of synthesis of the compounds of the invention.

The present invention also relates in yet a further aspect to pharmaceutical compositions comprising at least one compound of the present invention and a pharmaceutically acceptable carrier, and optionally at least one further therapeutically active agent.

In yet another aspect, the present invention relates to methods for the treatment or prevention of disorders, diseases, or conditions responsive to the modulation of the ROR gamma receptor in a mammal in need thereof, in particular diabetes and diabetes-related disorders, specifically type II diabetes, by administering at least one compound (or a pharmaceutical composition thereof) of the present invention.

In yet a further aspect, the present invention relates to the kits comprising at least one compound of the present invention (or a pharmaceutical composition thereof).

DETAILED DESCRIPTION OF THE INVENTION

Figure 1:
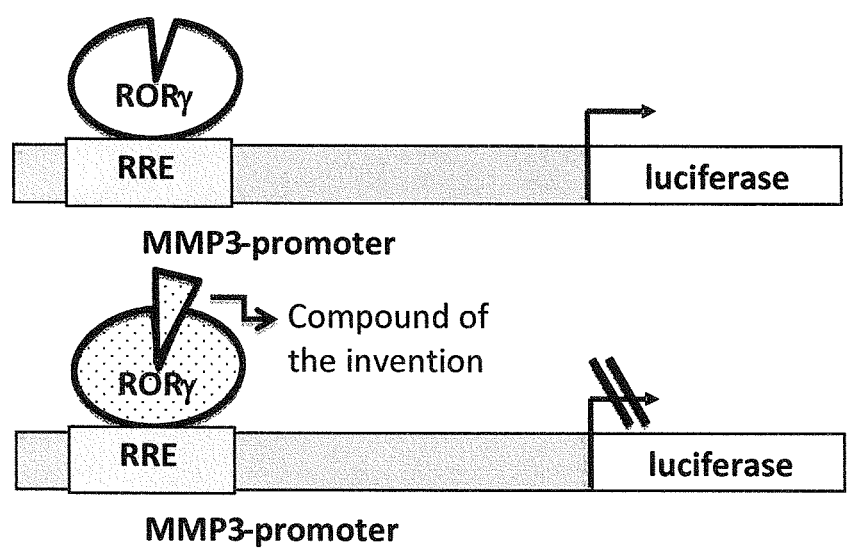
FIG. 1. Schematic of the luciferase activity assay

Unless specified otherwise, the following terms have the indicated meanings:

The term "subject" means a mammal, such as a human or an animal, being either male or female, preferably a human.

The term "ligand" or "modulator" refers to a natural or synthetic compound which binds a receptor molecule to form a receptor-ligand complex. The term ligand may include agonists, antagonists, and compounds with partial agonist/antagonist action. An "agonist" is a natural or synthetic compound which binds the receptor to form a receptor-agonist complex thereby activating said receptor, initiating a pathway signaling and further biological processes. By "antagonist" is meant a natural or synthetic compound that has a biological effect opposite to that of an agonist. An antagonist binds the receptor and blocks the action of a receptor agonist. The term "ligand" or "modulator", when used according to the present invention in combination with e.g. a ROR (gamma) receptor, refers to a(n) (endogenous) compound that can interact with a ROR (gamma) receptor and initiate a pharmacological or biochemical response.

The term "binding affinity" refers to the ability of a compound to bind to its biological target. For the present invention, it refers to the ability of a compound of the invention, to bind to the ROR (gamma) receptor.

The term "efficacy" describes the relative intensity of response induced by a compound when binding to its receptor. Maximal response depends on the efficiency of coupling to the receptor.

The term "diabetes" as used herein includes both insulin-dependent diabetes mellitus (i.e., IDDM, also known as type I diabetes) and non-insulin-dependent diabetes mellitus (i.e., NIDDM, also known as type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. The compounds and compositions of the present invention may be useful for treating both type I and type II diabetes, but may be especially effective for treating type II diabetes (as shown hereinafter).

The term "diabetes related disorders" as used herein includes diseases, disorders and conditions that are related to type 1 and type 2 diabetes, in particular diseases, disorders and conditions that are related to type 2 diabetes, and therefore may be treated, controlled or in some cases prevented, by administration of the compounds and compositions of this invention. Diabetes related disorders include e.g. hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, neuropathy, Syndrome X, ovarian hyperandrogenism (polycystic ovarian syndrome), and other disorders where insulin resistance is a contributive component.

"Treatment" of diabetes according to the invention refers to the administration of at least one compound of the present invention to treat diabetes and diabetes-related disorders as defined herein, e.g. in a subject in need thereof, e.g. a diabetic subject. Possible outcomes of such treatment may be decreasing the glucose level in a subject with elevated glucose levels and/or improving glycemic control and/or decreasing insulin levels in a subject with elevated insulin levels and/or to reduce an increased plasma glucose concentration and/or to reduce an increased insulin concentration and/or to reduce an increased blood triglyceride concentration and/or to increase insulin sensitivity and/or enhancing glucose tolerance in a subject with glucose intolerance and/or to reduce insulin resistance and/or to lower plasma insulin levels and/or an improvement in glycemic control, particularly in type 2 diabetes.

"Prevention" (or "prophylaxis") of diabetes according to the invention refers to the administration of at least one compound of the present invention to prevent or treat the onset of diabetes and diabetes-related disorders as defined herein in a subject in need thereof, e.g. a prediabetic subject.

The term "subject" as used herein refers to an animal, preferably a mammal, most preferably a human.

The term "polyhydroxylated cholane skeleton" includes in particular polyhydroxylated cholestanes and more specifically polyhydroxylated bile acids. A polyhydroxylated cholane or bile acid compound according to the invention includes, but is not limited to, from trihydroxylated, tetrahydroxylated, pentahydroxylated, hexahydroxylated bile acids, etc., up to the maximal hydroxylation level, but preferably (at least) trihydroxylated and (at least) tetrahydroxylated bile acids. The term "bile acid" encompasses all naturally occurring (chemically synthesized) bile acids (whether from man or from another animal) including conjugates thereof (e.g. in particular conjugates with glycine, taurine and possibly other amino acids), as well as synthetic or semi-synthetic analogs. Most naturally occurring bile acids are characterized by hydroxyl groups in the A, B, and C ring of the cholane skeleton, predominantly at one or more of positions C3, C7, C12, possibly (but more unusual) at positions C1, C6 and others. The junction of rings A and B in the cholane skeleton (and in bile acids) exists in two isomeric forms, i.e. the C5- and C8-substituents are cis (5-beta-cholane) or trans (5-alpha-cholane) configured. For the compounds of the present invention, if not specified differently, both the alpha- and beta-isomer of the A/B-ring junction are contemplated, preferably the beta-isomer.

The present invention relates in a first aspect to compounds for use as modulators of the ROR receptor, in particular, as selective ROR gamma receptor ligands, having the general formula I or pharmaceutically acceptable salts or stereoisomers thereof (numbering according to IUPAC nomenclature rules is indicated)

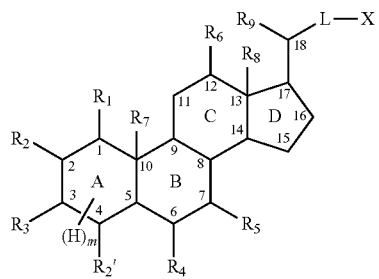

I wherein $R_1$, $R_2$, $R_{2'}$ are independently of each other hal, —$OR_a$, —$SR_a$, —$NR_aR_b$, —$COOR_a$, —$CONR_aR_b$, wherein $R_a$ and $R_b$ are independently of each other H or (C1-6)alkyl, or $R_1$, $R_2$ form together with the C-atoms to which they are linked an epoxy group;

$R_3$, $R_4$, $R_5$, $R_6$, are independently of each other H, hal, —$OR_a$, —$SR_a$, —$NR_aR_b$, —$COOR_a$, —$CONR_aR_b$, oxo, thio wherein $R_a$ and $R_b$ are independently of each other H or (C1-6)alkyl;

$R_7$, $R_8$, $R_9$ are independently of each other H, (C1-10)alkyl, wherein one or more non neighbouring $CH_2$ groups may be replaced with —O—, —S—, —CO—, —CO—O—, —O—CO—, —$NR_a$—, —CO—$NR_a$—, —$NR_a$—CO—, —C=C—, or —C≡C—; wherein $R_a$ is H or (C1-6)alkyl;

L is a linking group, such as straight-chain or branched C(1-12)alkyl, which is unsubstituted or substituted by at least one CN, hal, OH, $NR_aR_b$, $COOR_a$, $NO_2$, and wherein one or more of the non-adjacent $CH_2$ groups may independently be replaced by a group selected from —O—, —CO—, —CO—O—, —O—CO—, —$NR_a$—, —$NR_a$—CO—, —CO—$NR_a$—, —CH=CH—, —C≡C—, wherein $R_a$ and $R_b$ are independently of each other H or C(1-6)alkyl, X is H, —$OR_a$, —$SR_a$, —$NR_aR_b$, —$COOR_c$, —$CONR_aR_c$; wherein $R_a$ and $R_b$ are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl;

m is 0 to 5.

It is understood, that $(H)_m$ represents all hydrogen substituents on the indicated A-ring (i.e. on C1, C2, C3, C4, C5 and C10). The skilled person will know how many H-substituents are present for a specific substitution pattern of groups $R_1$, $R_2$, $R_{2'}$, $R_3$ on ring A. For example, m=5 may represent a fully saturated ring having no double bonds, m=3 may represent e.g. a ring having one double bond (between e.g. C1-C2 or between C4-C5), m=2 may represent e.g. a ring having one double bond (between e.g. C1-C2 or between C4-C5) and $R_3$ being oxo, and m=0 may represent e.g. a fully unsaturated ring having double bonds between C1-C2 and between C4-C5 and $R_3$ being oxo. Thus the degree of unsaturation and nature of substituents determines the number of H-atoms present or vice versa, the number of H-atoms is a way to indicate the degree of unsaturation of ring A.

In specific embodiments, the compounds of the invention according to formula I are based on a polyhydroxylated cholane skeleton having a -L-X-substituent at C17, and wherein the hydroxyl (or oxo-) substituents are preferably in two or more, preferably at least three, positions selected from C1, C3, C6, C7, C12 (represented by groups $R_1$, $R_3$, $R_4$, $R_5$, $R_6$, respectively), more preferably wherein the hydroxyl (or oxo-) substituents are at a total of three or four positions selected from C1, C3, C6, C7, C12, most preferably wherein the hydroxyl (or oxo-) substituents are at a total of three or four positions selected from C1, C3, C6, C7, C12 of which one hydroxyl (or oxo-) substituent is in position C1 or C6.

Thus, in some embodiments, the compounds of the invention have three hydroxyl (or oxo-substituents) and the hydroxylation patterns include (i) a hydroxyl (or oxo-) substituent at C1 in combination with following combinations of two further hydroxyl (or oxo-) substituents at positions C3 and C7, C3 and C12, C7 and C12, and (ii) a hydroxyl (or oxo-) substituent at C6 in combination with following combinations of two further hydroxyl (or oxo-) substituents at positions C3 and C7, C3 and C12, and C7 and C12, and (iii) a hydroxyl (or oxo-) substituent at both C1 and C6 in combination with a further hydroxyl (or oxo-) substituent at position C3 or C7 or C12.

In other embodiments, the compounds of the invention have four hydroxyl (or oxo-) substituents and the hydroxylation patterns include (i) a hydroxyl (or oxo-) substituent at C1 in combination with three further hydroxyl (or oxo-) substituents at positions C3, C7 and C12; (ii) a hydroxyl (or oxo-) substituent at C6 in combination with three further hydroxyl (or oxo-) substituents at positions C3, C7 and C12 and (iii) a hydroxyl (or oxo-) substituent at positions C1 and C6 in combination with following combinations of two further hydroxyl (or oxo-) substituents at positions C3 and C7; C3 and C12; C7 and C12.

In a preferred embodiment, $R_7$, $R_8$, $R_9$ are independently of each other H, (C1-10)alkyl, more preferably methyl, ethyl, propyl, butyl, most preferably methyl.

In some embodiments, $R_1$, $R_2$ are independently of each other H, hal, —$OR_a$, —$COOR_a$, wherein $R_a$ is H or (C1-6)alkyl, or form together with the C-atoms to which they are linked an epoxy group.

Preferably, $R_2$ is H or hal, or forms together with $R_1$ and the C-atoms to which $R_1$ and $R_2$ are linked an epoxy group.

Preferably $R_{2'}$ is H or hal, more preferably H or Cl, Br, I.

Preferably, $R_3$, $R_4$, $R_5$, $R_6$ are independently of each other H, —$OR_a$, —$NR_aR_b$, —$COOR_a$, —$CONR_aR_b$ or oxo, wherein $R_a$ and $R_b$ are independently of each other H or (C1-6)alkyl.

More preferably $R_3$, is H, —$OR_a$, —$NR_aR_b$ or oxo, wherein $R_a$ and $R_b$ are independently of each other H or (C1-6)alkyl; $R_4$, $R_5$, $R_6$ are independently of each other H, —$OR_a$ or —$NR_aR_b$, wherein $R_a$ and $R_b$ are independently of each other H or (C1-6)alkyl; and $R_7$, $R_8$, $R_9$ are independently of each other H, (C1-10)alkyl, more preferably methyl, ethyl, propyl, butyl, most preferably methyl.

Thus, preferably, the invention includes compounds of formula II and pharmaceutically acceptable salts or stereoisomers thereof, preferably its stereoisomeric form IIa,

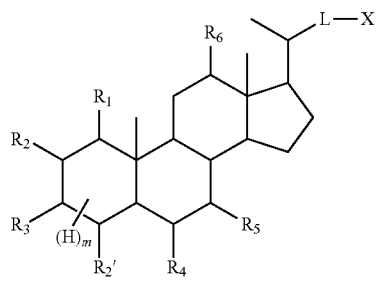

II

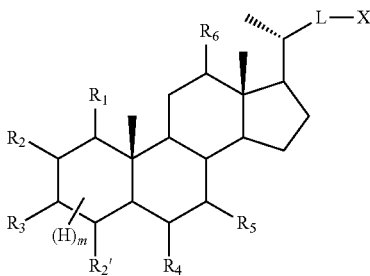

IIa wherein $R_1$, $R_2$ are independently of each other H, hal, —$OR_a$, —$SR_a$, —$NR_aR_b$, —$COOR_a$, —$CONR_aR_b$, wherein $R_a$ and $R_b$ are independently of each other H or (C1-6)alkyl, or $R_1$, $R_2$ form together with the C-atoms to which they are linked an epoxy group;

$R_3$, $R_4$, $R_5$, $R_6$, are independently of each other H, hal, —$OR_a$, —$SR_a$, —$NR_aR_b$, —$COOR_a$, —$CONR_aR_b$, oxo, thio wherein $R_a$ and $R_b$ are independently of each other H or (C1-6)alkyl;

$R_{2'}$ is H or hal,

L is a linking group, such as straight-chain or branched C(1-12)alkyl, which is unsubstituted or substituted by at least one CN, hal, OH, $NR_aR_b$, $COOR_a$, $NO_2$, and wherein one or more of the non-adjacent $CH_2$ groups may independently be replaced by a group selected from —O—, —CO—, —CO—O—, —O—CO—, —$NR_a$—, —$NR_a$—CO—, —CO—$NR_a$—, —CH=CH—, —C≡C—, wherein $R_a$ and $R_b$ are independently of each other H or C(1-6)alkyl, X is H, —$OR_a$, —$SR_a$, —$NR_aR_b$, —$COOR_c$, —$CONR_aR_c$; wherein $R_a$ and $R_b$ are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl;

m is 0 to 5.

In a preferred embodiment, at least three groups, preferably three or four groups, selected from $R_1$, $R_3$, $R_4$, $R_5$ and $R_6$ are —$OR_a$ or oxo, wherein $R_a$ is H or C(1-6)alkyl.

In another preferred embodiment, $R_1$ and/or $R_4$ are —$OR_a$ or oxo.

More preferably, at least three groups, preferably three or four groups, selected from $R_1$, $R_3$, $R_4$, $R_5$ and $R_6$ are —$OR_a$ or oxo, with the proviso that $R_1$ and/or $R_4$ are —$OR_a$ or oxo, wherein $R_a$ is H or C(1-6)alkyl.

In specific embodiments L (in all of the formulas disclosed herein) is a straight-chain or branched C(1-12)alkyl, which is unsubstituted and wherein one or more of the non-adjacent $CH_2$ groups may independently be replaced by a group selected from —O—, —CO—, —CO—O—. Preferably L is straight-chain or branched C(1-12)alkyl, more preferably a straight-chain or branched C(1-6)alkyl as defined herein.

Preferably, X (in all of the formulas disclosed herein) is H, —$OR_a$, —$COOR_c$, —$CONR_aR_c$, wherein $R_a$ is H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl. Preferably, $R_c$ is —H, —(C1-6)alkyl, —NH—$CH_2$—$CO_2R_a$ or —NH—$(CH_2)_2$—$SO_3R_a$, wherein $R_a$ is —H or —(C1-6)alkyl.

In preferred embodiments, group -L-X (in all of the formulas disclosed herein) is —(C1-6)alkyl-$COOR_a$, more preferably —$(CH_2)_2$—$COOR_a$, wherein $R_a$ is —H or —(C1-6)alkyl.

Preferably, $R_2$ is H or hal, or forms together with $R_1$ and the C-atoms to which $R_1$ and $R_2$ are linked an epoxy group.

In specific embodiments, $R_4$, $R_6$, are —$OR_a$, thus the invention specifically includes compounds of formula IIIa, and all pharmaceutically acceptable salts or stereoisomers thereof, preferably its stereoisomeric form IIIb

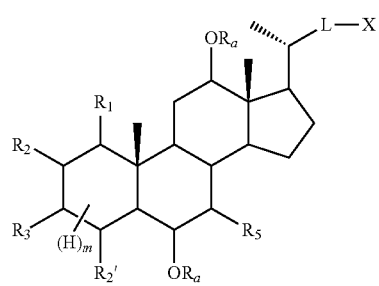

IIIa

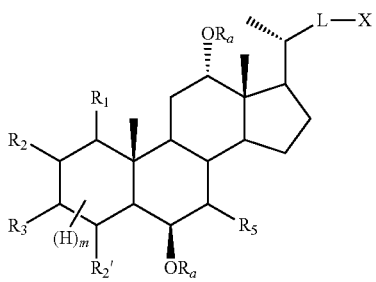

IIIb wherein $R_1$ is H, hal, —$OR_a$, —$SR_a$, —$NR_aR_b$, —$COOR_a$, —$CONR_aR_b$, preferably H, —$OR_a$, —$NR_aR_b$, wherein $R_a$ and $R_b$ are independently of each other H or (C1-6)alkyl, or $R_1$ forms together with $R_2$ and the C-atoms to which $R_1$, $R_2$ are linked to an epoxy group;

$R_2$ is H, hal, —$OR_a$, —$SR_a$, —$NR_aR_b$, —$COOR_a$, —$CONR_aR_b$, preferably H or hal, wherein $R_a$ and $R_b$ are independently of each other H or (C1-6)alkyl, or $R_2$ forms together with $R_1$ and the C-atoms to which $R_1$, $R_2$ are linked to an epoxy group;

$R_3$, $R_5$ are independently of each other H, hal, —$OR_a$, —$SR_a$, —$NR_aR_b$, —$COOR_a$, —$CONR_aR_b$, oxo, thio, preferably H, oxo, —$OR_a$, —$NR_aR_b$, wherein $R_a$ and $R_b$ are independently of each other H or (C1-6)alkyl;

$R_{2'}$ is H or hal,

L is a straight-chain or branched C(1-12)alkyl, which is unsubstituted and wherein one or more of the non-adjacent $CH_2$ groups may independently be replaced by a group selected from —O—, —CO—, —CO—O;

X is H, —$OR_a$, —$SR_a$, —$NR_aR_b$, —$COOR_c$, —$CONR_aR_c$; wherein $R_a$ and $R_b$ are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl;

$R_a$ is H or C(1-6)alkyl;

m is 0 to 5.

In other specific embodiments, $R_6$ is —$OR_a$ and $R_1$ is either —$OR_a$ or forms with $R_2$ an epoxide, and thus the invention specifically includes compounds of formula IIIc and IIId, and all pharmaceutically acceptable salts or stereoisomers thereof, preferably its stereoisomeric forms IIIe$_1$/IIIe$_2$ and IIIf$_1$/IIIf$_2$

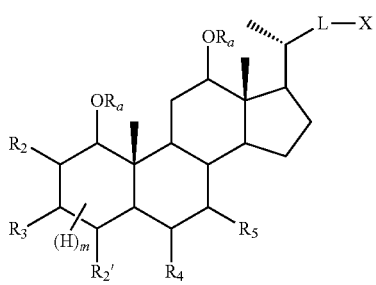

IIIc

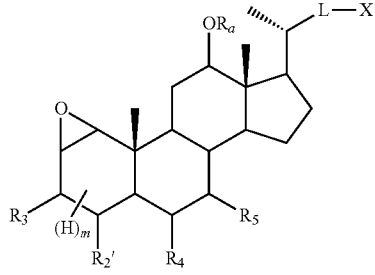

IIId

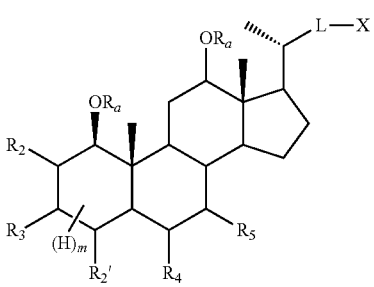

IIIe$_1$

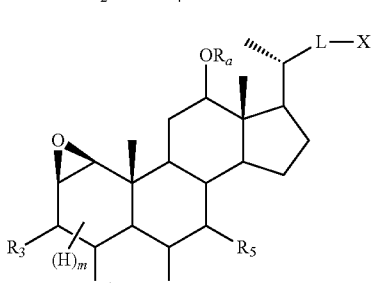

IIIf$_1$

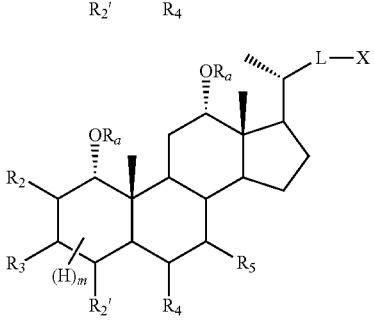

IIIe$_2$

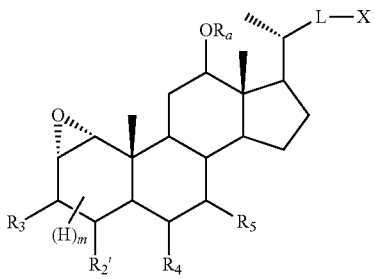

IIIf$_2$ wherein $R_2$ is H, hal, —$OR_a$, —$SR_a$, —$NR_aR_b$, —$COOR_a$, —$CONR_aR_b$, preferably H or hal, wherein $R_a$ and $R_b$ are independently of each other H or (C1-6)alkyl;

$R_3$, $R_4$, $R_5$ are independently of each other H, hal, —$OR_a$, —$SR_a$, —$NR_aR_b$, —$COOR_a$, —$CONR_aR_b$, oxo, thio, preferably H, oxo, —$OR_a$, —$NR_aR_b$, wherein $R_a$ and $R_b$ are independently of each other H or (C1-6)alkyl;

$R_{2'}$ is H or hal,

L is a straight-chain or branched C(1-12)alkyl, which is unsubstituted and wherein one or more of the non-adjacent $CH_2$ groups may independently be replaced by a group selected from —O—, —CO—, —CO—O;

X is H, —$OR_a$, —$SR_a$, —$NR_aR_b$, —$COOR_c$, —$CONR_aR_c$; wherein $R_a$ and $R_b$ are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl;

$R_a$ is H or C(1-6)alkyl, m is 0 to 5.

In specific embodiments, $R_3$ is —$OR_a$ and $R_6$ is either —$OR_a$ or oxo, and thus the invention specifically includes compounds of formula IIIg and IIIh, and all pharmaceutically acceptable salts or stereoisomers thereof, preferably its stereoisomeric forms IIIi$_1$, IIIi$_2$

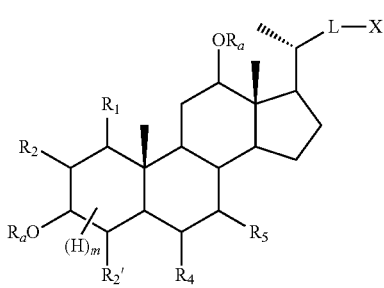

IIIg

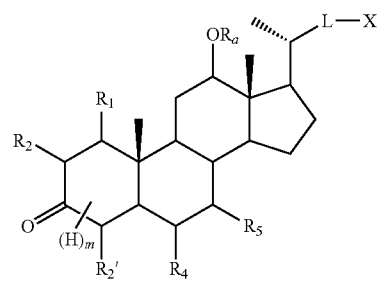

IIIh

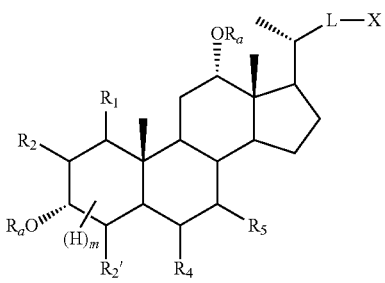

IIIi$_1$

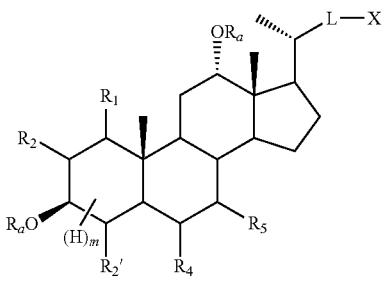

IIIi$_2$ wherein $R_1$ is H, hal, —$OR_a$, —$SR_a$, —$NR_aR_b$, —$COOR_a$, —$CONR_aR_b$, preferably H, —$OR_a$, —$NR_aR_b$, wherein $R_a$ and $R_b$ are independently of each other H or (C1-6)alkyl, or $R_1$ forms together with $R_2$ and the C-atoms to which $R_1$, $R_2$ are linked to an epoxy group;

$R_2$ is H, hal, —$OR_a$, —$SR_a$, —$NR_aR_b$, —$COOR_a$, —$CONR_aR_b$, preferably H or hal, wherein $R_a$ and $R_b$ are independently of each other H or (C1-6)alkyl, or $R_2$ forms together with $R_1$ and the C-atoms to which $R_1$, $R_2$ are linked to an epoxy group;

$R_4$, $R_5$ are independently of each other H, hal, —$OR_a$, —$SR_a$, —$NR_aR_b$, —$COOR_a$, —$CONR_aR_b$, oxo, thio, preferably H, oxo, —$OR_a$, —$NR_aR_b$, wherein $R_a$ and $R_b$ are independently of each other H or (C1-6)alkyl;

$R_{2'}$ is H or hal,

L is a straight-chain or branched C(1-12)alkyl, which is unsubstituted and wherein one or more of the non-adjacent $CH_2$ groups may independently be replaced by a group selected from —O—, —CO—, —CO—O;

X is H, —$OR_a$, —$SR_a$, —$NR_aR_b$, —$COOR_c$, —$CONR_aR_c$; wherein $R_a$ and $R_b$ are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl;

$R_a$ is H or C(1-6)alkyl, m is 0 to 5.

In specific embodiments, $R_5$, $R_6$ are —$OR_a$, thus the invention specifically includes compounds of formula IIIj, and all pharmaceutically acceptable salts or stereoisomers thereof, preferably its stereoisomeric form IIIk

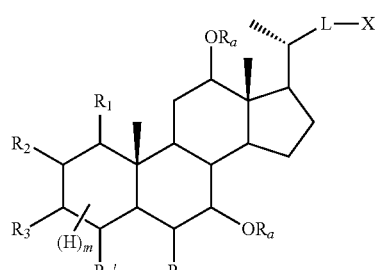

IIIj

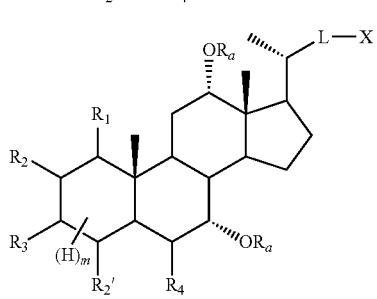

IIIk wherein $R_1$ is H, hal, —$OR_a$, —$SR_a$, —$NR_aR_b$, —$COOR_a$, —$CONR_aR_b$, preferably H, —$OR_a$, —$NR_aR_b$, wherein $R_a$ and $R_b$ are independently of each other H or (C1-6)alkyl, or $R_1$ forms together with $R_2$ and the C-atoms to which $R_1$, $R_2$ are linked to an epoxy group;

$R_2$ is H, hal, —$OR_a$, —$SR_a$, —$NR_aR_b$, —$COOR_a$, —$CONR_aR_b$, preferably H or hal, wherein $R_a$ and $R_b$ are independently of each other H or (C1-6)alkyl, or $R_2$ forms together with $R_1$ and the C-atoms to which $R_1$, $R_2$ are linked to an epoxy group;

$R_3$, $R_4$, are independently of each other H, hal, —$OR_a$, —$SR_a$, —$NR_aR_b$, —$COOR_a$, —$CONR_aR_b$, oxo, thio, preferably H, oxo, —OR$_a$, —NR$_a$R$_b$, wherein R$_a$ and R$_b$ are independently of each other H or (C1-6)alkyl;

R$_{2'}$ is H or hal,

L is a straight-chain or branched C(1-12)alkyl, which is unsubstituted and wherein one or more of the non-adjacent CH$_2$ groups may independently be replaced by a group selected from —O—, —CO—, —CO—O;

X is H, —OR$_a$, —SR$_a$, —NR$_a$R$_b$, —COOR$_c$, —CONR$_a$R$_c$; wherein R$_a$ and R$_b$ are independently of each other H or (C1-6)alkyl and R$_c$ is —H, —(C1-6)alkyl, —NH—(CH$_2$)$_n$—CO$_2$R$_a$ or —NH—(CH$_2$)$_p$—SO$_3$R$_a$, wherein n, p is 1, 2, or 3 and R$_a$ is —H or —(C1-6)alkyl;

R$_a$ is H or C(1-6)alkyl, m is 0 to 5.

In specific embodiments, R$_1$ is —OR$_a$, in compound of formula IIIa (and stereoisomeric forms thereof), or R$_4$ is —OR$_a$ in compounds of formula IIIc and IIId (and stereoisomeric forms thereof), or both R$_1$ and R$_4$, are —OR$_a$ in compounds of formula IIIg, IIIh, and IIIk (and stereoisomeric forms thereof), wherein R$_a$ is H or (C1-6)alkyl.

In preferred embodiments the invention includes compounds of formula IV (wherein R$_3$ is oxo) and all pharmaceutically acceptable salts or stereoisomers thereof,

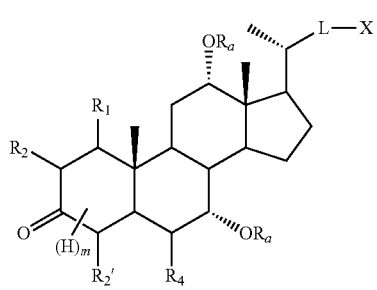

IV wherein

R$_1$ is H, hal, —OR$_a$, —SR$_a$, —NR$_a$R$_b$, —COOR$_a$, —CONR$_a$R$_b$, preferably H, —OR$_a$, —NR$_a$R$_b$, wherein R$_a$ and R$_b$ are independently of each other H or (C1-6)alkyl, or R$_1$ forms together with R$_2$ and the C-atoms to which R$_1$, R$_2$ are linked to an epoxy group;

R$_2$ is H or hal, or R$_2$ forms together with R$_1$ and the C-atoms to which R$_1$, R$_2$ are linked to an epoxy group;

R$_{2'}$ is H or hal,

R$_4$ is H, hal, —OR$_a$, —SR$_a$, —NR$_a$R$_b$, —COOR$_a$, —CONR$_a$R$_b$, oxo, thio, preferably H, oxo, —OR$_a$, —NR$_a$R$_b$, wherein R$_a$ and R$_b$ are independently of each other H or (C1-6)alkyl, L is a straight-chain or branched C(1-12)alkyl;

X is H, —OR$_a$, —COOR$_c$, —CONR$_a$R$_c$, wherein R$_a$ is H or (C1-6)alkyl and R$_c$ is —H, —(C1-6)alkyl, —NH—(CH$_2$)$_n$—CO$_2$R$_a$ or —NH—(CH$_2$)$_p$—SO$_3$R$_a$, wherein n, p is 1, 2, or 3 and R$_a$ is —H or —(C1-6)alkyl, R$_a$ is H or C(1-6)alkyl, and m is 1, 2, 3 or 4.

Preferably, m is 4, if ring A is fully saturated, and m is 0 or 2, if ring A is partially (one double bond) or fully (two double bonds) unsaturated.

In a preferred embodiment, R$_1$ or R$_4$ or both R$_1$ and R$_4$ in compound IV are —OR$_a$, wherein R$_a$ is H or (C1-6)alkyl.

In other preferred embodiments the invention includes compounds of formula V (wherein R$_3$ is —OR$_a$) and all pharmaceutically acceptable salts or stereoisomers thereof, preferably its stereoisomeric forms Va and Vb

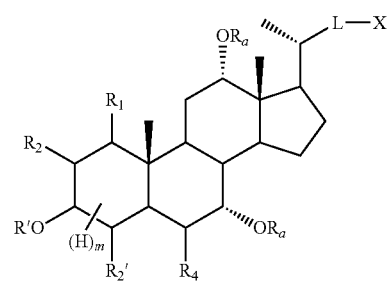

V

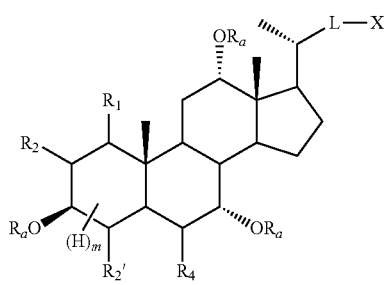

Va

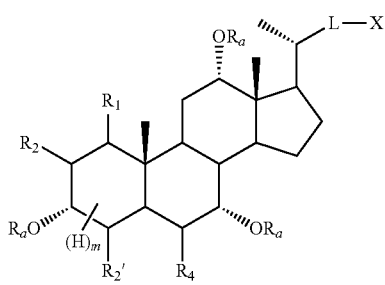

Vb wherein

R$_1$ is H, hal, —OR$_a$, —SR$_a$, —NR$_a$R$_b$, —COOR$_a$, —CONR$_a$R$_b$, preferably H, —OR$_a$, —NR$_a$R$_b$, wherein R$_a$ and R$_b$ are independently of each other H or (C1-6)alkyl, or R$_1$ forms together with R$_2$ and the C-atoms to which R$_1$, R$_2$ are linked to an epoxy group;

R$_2$ is H or hal, or R$_2$ forms together with R$_1$ and the C-atoms to which R$_1$, R$_2$ are linked to an epoxy group;

R$_{2'}$ is H or hal,

R$_4$ is H, hal, —OR$_a$, —SR$_a$, —NR$_a$R$_b$, —COOR$_a$, —CONR$_a$R$_b$, oxo, thio, preferably H, oxo, —OR$_a$, —NR$_a$R$_b$, wherein R$_a$ and R$_b$ are independently of each other H or (C1-6)alkyl, L is a straight-chain or branched C(1-12)alkyl;

X is H, —OR$_a$, —COOR$_c$, —CONR$_a$R$_c$, wherein R$_a$ is H or (C1-6)alkyl and R$_c$ is —H, —(C1-6)alkyl, —NH—(CH$_2$)$_n$—CO$_2$R$_a$ or —NH—(CH$_2$)$_p$—SO$_3$R$_a$, wherein n, p is 1, 2, or 3 and R$_a$ is —H or —(C1-6)alkyl, R$_a$ is H or C(1-6)alkyl, and m is 1, 2, 3, 4 or 5.

Preferably, m is 5, if ring A is fully saturated, and m is 1 or 3, if ring A is partially (one double bond) or fully (two double bonds) unsaturated.

In a preferred embodiment, R$_1$ or R$_4$ or both R$_1$ and R$_4$ in any of compounds of formula V, Va, and Vb are —OR$_a$, wherein R$_a$ is H or (C1-6)alkyl.

Some preferred examples include e.g. compounds with R$_3$=—OR$_a$, R$_1$=R$_2$=R$_{2'}$=H, and R$_4$ is —OR$_a$ of formula VIa, and all pharmaceutically acceptable salts or stereoisomers thereof, which includes the C3α- and C3β-stereoisomer (VIa$_1$, VIa$_2$); or compounds with R₃ being —OR$_a$, R₄=R$_2$=R$_{2'}$=H, and R₁ is —OR$_a$, of formula VIb, and all pharmaceutically acceptable salts or stereoisomers thereof, which includes the C1α/C3α-, C1α/C3α-, C1β/C3α-, C1β/C3β-stereoisomer (VIb₁, VIb₂, VIb₃, VIb₄); or compounds with R₃ being —OR$_a$, R$_2$=R$_{2'}$=H, and R₁ and R₄ are —OR$_a$, of formula VIc, which includes the C1α/C3α-, C1α/C3β-, C1β/C3α-, C1β/C3β-stereoisomer each of them with C6 either in α or in β-position.

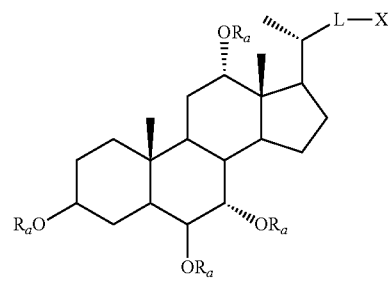

VIa

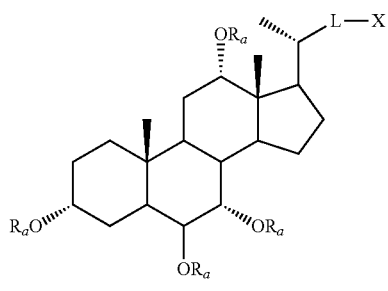

VIa₁

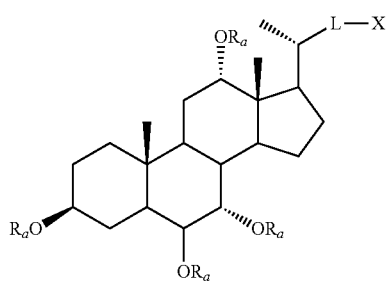

VIa₂

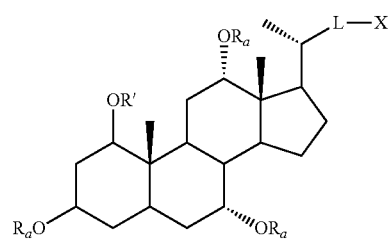

VIb

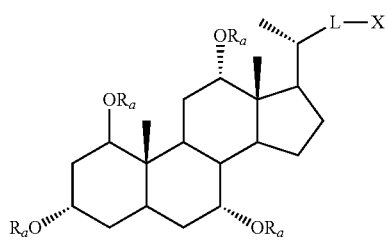

VIb₁

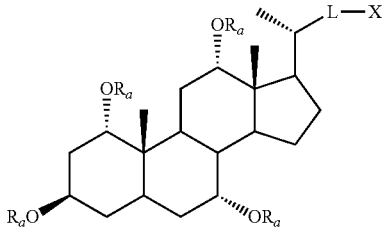

VIb₂

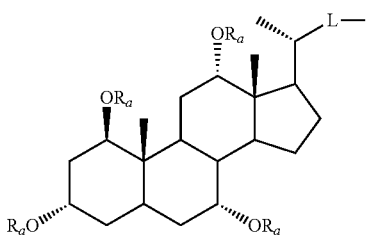

VIb₃

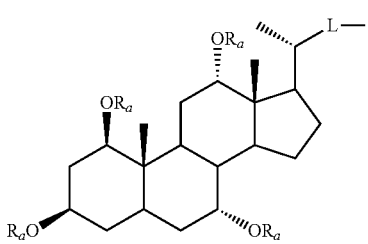

VIb₄

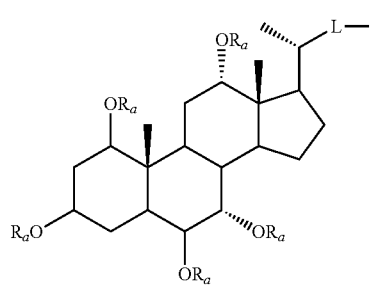

VIc wherein L is a straight-chain or branched C(1-12)alkyl, which is unsubstituted and wherein one or more of the non-adjacent CH₂ groups may independently be replaced by a group selected from —O—, —CO—, —CO—O—, preferably straight-chain or branched C(1-6)alkyl, R$_a$ is H or C(1-6)alkyl, X is H, —OR$_a$, —SR$_a$, —NR$_a$R$_b$, —COOR$_c$, —CONR$_a$R$_c$; wherein R$_a$ and R$_b$ are independently of each other H or (C1-6)alkyl and R$_c$ is —H, —(C1-6)alkyl, —NH—(CH₂)$_n$—CO₂R$_a$ or —NH—(CH₂)$_p$—SO₃R$_a$, wherein n, p is 1, 2, or 3 and R$_a$ is —H or —(C1-6)alkyl, preferably H, —OR$_a$, —COOR$_c$, —CONR$_a$R$_c$.

Other preferred examples include e.g. compounds with R₃=oxo, R₁=R₂=R$_{2'}$=H, R₄ is —OR$_a$ and ring A is partially unsaturated of formula VIIa, VIIb, and all pharmaceutically acceptable salts or stereoisomers thereof, which includes the C6□- or C6□-stereoisomer;

compounds with R₃=oxo, R₄=R$_{2'}$, and either R₁ is —OR$_a$ and R₂ is H or R₁ and R₂ from an epoxide, of formula VIIc, VIId, and all pharmaceutically acceptable salts or stereoisomers thereof, which includes the C1□- or C1□-stereoisomer (of the epoxide or —OR$_a$; and compounds with R₃=oxo, R$_{2'}$=H, both R₁ and R₄ are —OR$_a$ or oxo, and ring A is saturated or partially unsaturated of formula VIIe, VIIf, and all pharmaceutically acceptable salts or stereoisomers thereof, which includes the C1α/C6α-, C1α/C6β-, C1β/C6α-, C1β/C6β-stereoisomer, VIIa
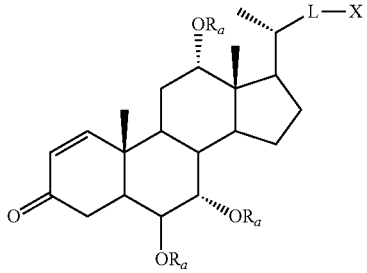

VIIb
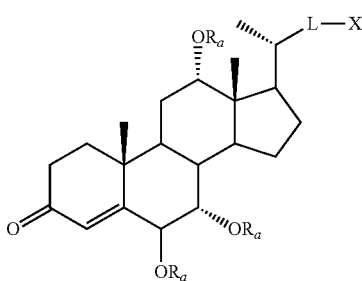

VIIc
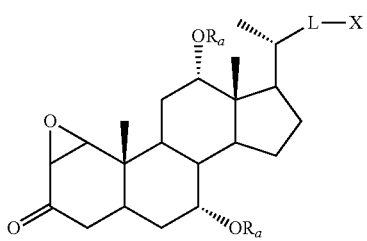

VIId
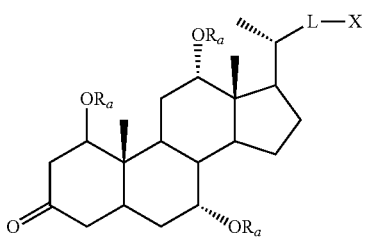

VIIe
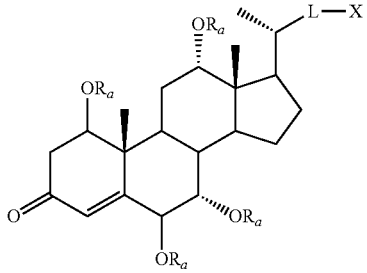

-continued

VIIf
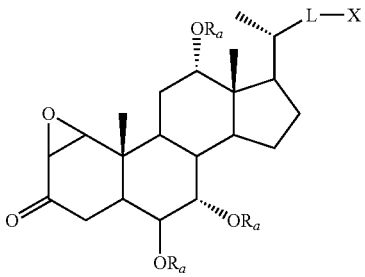

wherein L is a straight-chain or branched C(1-12)alkyl, which is unsubstituted and wherein one or more of the non-adjacent $CH_2$ groups may independently be replaced by a group selected from —O—, —CO—, —CO—O—, preferably straight-chain or branched C(1-6)alkyl, $R_a$ is H or C(1-6)alkyl, X is H, —$OR_a$, —$SR_a$, —$NR_aR_b$, —$COOR_c$, —$CONR_aR_c$; wherein $R_a$ and $R_b$ are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl, preferably H, —$OR_a$, —$COOR_c$, —$CONR_aR_c$.

The term "alkyl" refers to a straight chain or branched carbon chain comprising the specified number of carbon atoms. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, n-decyl and the like.

Thus the term "C(1-6)alkyl" as used herein refers to branched or straight alkyl groups and includes "linear C(1-6)alkyl", such as methyl, ethyl, n-propyl, n-butyl, n-pentyl and n-hexyl, and "branched C(3-6)alkyl", such as isopropyl, isobutyl, tert-butyl, 2-pentyl, 3-pentyl, 2-methylbutyl, 3-methylbutyl, 3-methyl-2-butyl, 2,2-dimethyl-propyl, 2-hexyl, 3-hexyl, 3-methyl-2-pentyl, 3-methyl-3-pentyl, 2,2-dimethyl-butyl, 3,3-dimethyl-butyl, 2,3-dimethyl-2-butyl, 2,3-dimethyl-3-butyl and 3,3-dimethyl-2-butyl.

The term "halogen" (or "hal") includes fluoro, chloro, bromo and iodo, preferably chloro and bromo, more preferably bromo.

The term "oxo" refers to an oxygen atom connected by a double bond (=O).

The term "thio" refers to a sulfur atom connected by a double bond (=S).

Index "m" is 1, 2, 3, 4, or 5.

It is understood that if one or more of the above defined terms occur more than once in a formula (e.g. $R_a$, $R_b$, $R_c$), each term is defined independently of the other.

The compounds of the invention may contain one chiral plane, one or more asymmetric or chiral centers and can exist in different stereoisomeric forms, such as racemates and racemic mixtures, optically pure enantiomers, enantiomeric mixtures, optically pure diastereomers and diastereomeric mixtures. All stereoisomeric forms of the intermediates and compounds of the present invention as well as mixtures thereof, including racemic and diastereomeric mixtures, which possess properties useful in the treatment of the conditions discussed herein, form a part of the present invention.

The compounds of the invention may be separated into their individual enantiomers and diastereoisomers by standard techniques known in the art, such as e.g. fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Enantiomers and diastereomers may be separated by use of a chiral HPLC column and by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Alternatively, any stereoisomer of a compound of the invention may be obtained by stereospecific synthesis using optically pure starting materials or reagents of known absolute configuration.

Such enenantiomeric or diastereomeric separation or stereospecific synthesis may be particularly desirable if enantiomers or diastereomers differ in biological activity.

The present invention is meant to comprehend all such isomeric forms of the compounds of the invention, including the E and Z geometric isomers of double bonds and mixtures thereof. A number of the compounds of the present invention and intermediates therefore exhibit tautomerism and therefore may exist in different tautomeric forms under certain conditions. The term "tautomer" or "tautomeric form" refers to structural isomers of equal energies (in 50:50 mixtures) or different energies which are interconvertible via a low energy barrier. For example, proton tautomers include interconversions via migration of a proton, such as keto-enol and imine-enamine isomerizations. Valence tautomers include interconversions by reorganization of some of the bonding electrons. All such tautomeric forms are within the scope of the invention. The depiction of any particular tautomeric form in any of the structural formulas herein is not intended to be limiting with respect to that form; but is meant to be representative of the entire tautomeric set.

It is further understood that the compounds of the present invention include hydrates, solvates, polymorphs, crystalline, hydrated crystalline and amorphous forms of the compounds of the present invention, and pharmaceutically acceptable salts thereof.

For example, the compounds of the present invention and intermediates may exist in unsolvated as well as solvated forms with solvents such as water, ethanol, isopropanol and the like, and both solvated and unsolvated forms are included within the scope of the invention. Solvates for use in the methods aspect of the invention should be with pharmaceutically acceptable solvents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, TEA, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic; maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids. It will be understood that, as used herein, references to the compounds of the invention are meant to also include the pharmaceutically acceptable salts, such as the hydrochloride salt.

In a further aspect the present invention also relates to methods of production of the compounds of the invention, which are able to overcome the disadvantages (e.g. poor yields) associated with the known prior art method. According to reported procedures a 1,3,7,12-tetrahydroxy compound is obtained by converting a suitably protected C3-oxo-cholic acid derivative into the corresponding enone, subsequently functionalizing the enone by nucleophilic epoxidation, followed by epoxide ring opening to give (after suitable deprotection schemes) the desired 1,3,7,12-tetrahydroxy compound.

It was found that particularly suitable methods for introduction of the hydroxyl functionality (e.g. at C1) include silicon based conjugate addition to a key intermediate enone and subsequent oxidative removal of the silicon group (under Tamao-Fleming conditions as described in e.g. Fleming, I. et al, J. Chem. Soc., Perkin Trans. 1, 1995, 317-337.), which enables obtaining the final intermediates in high yields and stereoselectivity.

Alternatively, Applicants have found that under specific conditions introduction of the hydroxyl functionality (e.g. at C1) may be achieved in good yields via epoxidation of the key intermediate enone if said enone is protected as a branched alkyl ester, such as the isopropylester (without significant hydrolysis of the ester functionality under basic conditions).

Furthermore, epoxide opening with lithium bromide alone or in combination with sodium triacetoxyborohydride (in place of alternative reagents including selenides or samarium iodide) gives the intermediate dibrominated ketone or alcohol respectively in high yields, which could be debrominated to provide the final key compounds using non-toxic and inexpensive reagents. Additionally, it was found that the reduction of all the hydroxyketones used in the syntheses, when performed with sodium triacetoxyborohydride afforded a single diastereoisomer (i.e. the anti diol) in contrast to epimeric mixtures obtained by the use of sodiumborohydride or other reducing agents.

The compounds of the invention are useful as effective ligands or modulators of the ROR receptor and in particular of the ROR gamma receptor. They are therefore useful for the treatment and/or prevention of disorders responsive to the modulation of the ROR gamma receptor, such as diabetes and diabetes-related disorders, and in particular type II diabetes.

Thus, the present invention also relates to the use of at least one compound of the invention as effective ligands or modulators of the ROR receptor and in particular of the ROR gamma receptor.

In particular, the present invention also relates to the use of at least one compound of the invention for the treatment or prevention, suppression or amelioration of a disease mediated by the ROR gamma receptor in a subject in need thereof.

More specifically, the present invention relates to the use of a therapeutically effective amount of at least one ROR gamma receptor ligand of formula I to VII, or a pharmaceutically acceptable salt or stereoisomer thereof, for the treatment or prevention, or suppression of a disease mediated by the ROR gamma receptor in a subject in need thereof, wherein the disease is selected from the group consisting of diabetes and diabetes-related disorders, in particular type II diabetes.

More specifically, the present invention relates to the use of a therapeutically effective amount of at least one compound of formula I to VII, or a pharmaceutically acceptable salt or stereoisomer thereof, for the treatment or prevention, or suppression of diabetes and/or diabetes-related disorders, in particular type II diabetes.

In some embodiments the compounds of the invention may be used singly, in other embodiments, the compounds of the invention may be used in combination with other compounds of the invention or in combination with other therapeutically active agents. Examples of other therapeutically active ingredients (for combined administration with one or more compounds of the invention) that may be useful for the treatment and/or prevention and/or amelioriation of the diseases or conditions for which the compounds of the invention are useful, i.e. diabetes and/or diabetes-related disorders, in particular type II diabetes, include, but are not limited to anti-diabetic agents, lipid-lowering agents, anti-hypertensive agents, and anti-obesity agents, such as the following:

(a) Anti-diabetic agents, for example, (1) glitazones (e.g., ciglitazone, darglitazone, englitazone, isaglitazon, pioglitazone, rosiglitazone, troglitazone, tularik, BRL49653, CLX-0921, 5-BTZD), and PPAR ligands such as GW-0207, LG-100641 and LY-300512; (2) biguanides such as buformin, metformin and phenformin; (3) protein tyrosine phosphatase-1B (PTP-1B) inhibitors; (4) sulfonylureas such as acetohexamide, chlorpropamide, diabinese, glibenclamide, glipizide, glyburide, glimepiride, gliclazide, glipentide, gliquidone, glisolamide, tolazamide and tolbutamide; (5) meglitinides such as repaglinide, nateglinide, and the like; (6) α-glucosidase inhibitors such as acarbose, adiposine, camiglibose, emiglitate, miglitol, voglibose, pradimicin-Q, salbostatin, CKD-711, MDL-25,637, MDL-73,945, and MOR14; (7) α-amylase inhibitors such as tendamistat, trestatin, and Al-3688; (8) insulin secretagogues such as linogliride, A-4166 and the like; (9) fatty acid oxidation inhibitors such as clomoxir, and etomoxir; (10) α-2 antagonists such as midaglizole, isaglidole, deriglidole, idazoxan, earoxan, and fluparoxan; (11) insulin and insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH$_2$; (12) non-thiazolidinediones such as JT-501, farglitazar (GW-2570/GI-262579), and muraglitazar; PPAR antagonists, such as muraglitazar, and the compounds disclosed in U.S. Pat. No. 6,414,002; (13) PPAR dual agonists such as MK-0767/KRP-297, CLX-0940, GW-1536, GW-1929, GW-2433, L-796449, LR-90, and SB219994; (14) other insulin sensitizers; (15) VPAC2 receptor agonists; (16) glucokinase activators; and (17) DPP-4 inhibitors, such as sitagliptin (JANUVIA™ sitagliptin), isoleucine thiazolidide (P32/98); NVP-DPP-728; vildagliptin (LAF 237); P93/01; denagliptin (GSK 823093), SYR322, RO 0730699, TA-6666, and saxagliptin (BMS 477118).

(b) lipid lowering agents, for example, (1) bile acid sequestrants such as cholestyramine, colesevelam, colestipol, dialkylaminoalkyl derivatives of a cross-linked dextran, Colestid®, LoCholest®, and Questran®, and the like; (2) HMG-CoA reductase inhibitors such as atorvastatin, itavastatin, fluvastatin, lovastatin, pitavastatin, pravastatin, rivastatin, rosuvastatin, and simvastatin, ZD-4522, and the like; (3) HMG-CoA synthase inhibitors; (4) cholesterol absorption inhibitors such as stanol esters, beta-sitosterol, sterol glycosides such as tiqueside, and azetidinones like ezetimibe; (5) acyl coenzyme A-cholesterol acyl-transferase (ACAT) inhibitors such as avasimibe, eflucimibe, KY505, and SMP797, and the like; (6) CETP inhibitors such as JTT705, torcetrapib, CP532632, BAY63-2149, SC591, and SC795, and the like; (7) squalene synthase inhibitors; (8) antioxidants such as probucol; (9) PPAR-a agoists such as beclofibrate, benzafibrate, ciprofibrate, clofibrate, etofibrate, fenofibrate, gemcabene, gemfibrozil, and other fibric acid derivatives, e.g., GW7647, BM170744, LY518674, Atromid®, Lopid®, and Tricor®, and compounds described in WO 97/36579, and the like; (10) FXR receptor modulators such as GW4064, SR103912, and the like; (11) LXR receptor ligands such as GW3965, T9013137, and XTC0179628, and the like; (12) lipoprotein synthesis inhibitors such as niacin; (13) renin/angiotensin system inhibitors; (14) PPAR-d partial agonists; (15) bile acid reabsorption inhibitors such as BARI1453, SC435, PHA384640, S8921, AZD7706, and the like; (16) PPAR-d agonists such as GW501516, GW590735, and compounds described in WO97/28149, and the like; (17) triglyceride synthesis inhibitors, (18) microsomal triglyceride transport (MTTP) inhibitors such as inplitapide, LAB687, and CP346086; (19) transcription modulators, (20) squalene epoxidase inhibitors; (21) low-density lipoprotein (LDL) receptor inducers; (22) platelet aggregation inhibitors; (23) 5-LO or FLAP inhibitors; and (24) niacin receptor agonists; and (c) anti-hypertensive agents, for example, (1) diuretics such as thiazides including chlorthalidone, chlorothiazide, dichlorphenamide, hydroflumethiazide, indapamide and hydrochlorothiazide; loop diuretics such as bumetanide, ethacrynic acid, furosemide, and torsemide; potassium sparing agents such as amiloride, triamterene; aldosterone antagonists such as spironolactone, and epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, and verapamil, and the like; (4) angiotensin converting enzyme (ACE) inhibitors such as benazepril, captopril, cilazapril, delapril, enalapril, fosinopril, imidapril, lisinopril, moexipril, quinapril, quinaprilat, ramipril, perindopril, perindropril, quanipril, spirapril, tenocapril, trandolapril, and zofenopril, and the like; (5) neutral endopeptidase inhibitors such as omapatrilat, cadoxatril, ecadotril, fosidotril, sampatrilat, AVE7688, ER4030, and the like; (6) endothelin antagonists such as bosentan, tezosentan, A308165, and YM62899, and the like; (7) vasodilators such as hydralazine, clonidine, minoxidil, and nicotinyl alcohol; (8) angiotensin II receptor antagonists such as candesartan, eprosartan, irbesartan, losartan, losartan and hydrochlorothiazide, pratosartan, tasosartan, telmisartan, valsartan, EXP-3137, FI6828K, and RNH6270, and the like; (9) a/beta-adrenergic blockers such as nipradilol, arotinolol, and amosulalol; (10) a1 blockers such as terazosin, urapidil, prazosin, bunazosin, trimazosin, doxazosin, naftopidil, indoramin, WHIP164, and XEN010; (11) a2 agonists such as lofexidine, tiamenidine, moxonidine, rilmenidine, and guanobenz; (12) aldosterone inhibitors; and (d) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) beta 3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate; (7) neuropeptide Y1 antagonists, such as BIBP3226, J-115814, BIBO 3304, LY-357897, CP-671906, GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A, and those disclosed in WO 01/96302, WO 01/68609, WO 02/51232, and WO 02/51838; (13) serotonin reuptake inhibitors such as fluoxetine, paroxetine, and sertraline; (14) melanocortin agonists, such as Melanotan II, CHIR86036 (Chiron), ME-10142, and ME-10145 (Melacure), CHIR86036 (Chiron); PT-141, and PT-14 (Palatin); (15) other MC4R (melanocortin 4 receptor) agonists; (16) 5HT-2 agonists; (17) 5HT2C (serotonin receptor 2C) agonists, such as BVT933, DPCA37215, WAY161503, R-1065; (18) galanin antagonists; (19) CCK agonists; (20) CCK-1 agonists (cholecystokinin-A) agonists, such as AR-R 15849, GI 181771, JMV-180, A-71378, A-71623 and SR146131; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl) carbamate, clobenpropit, iodophenpropit, imoproxifan, GT2394 (Gliatech), and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) beta-hydroxy steroid dehydrogenase-1 inhibitors (beta-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists; (30) leptin, including recombinant human leptin (PEG-OB, Hoffman La Roche) and recombinant methionyl human leptin (Amgen); (31) leptin derivatives; (32) other BRS3 (bombesin receptor subtype 3) agonists such as [D-Phe6,beta-Ala11,Phe13,Nle14]Bn(6 14) and [D-Phe6, Phe13]Bn(6-13)propylamid; (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone beta agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens; (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57)

11 beta HSD-1 (11-beta hydroxy steroid dehydrogenase type 1) inhibitors such as BVT 3498, BVT 2733; and other compounds such as aminorex; amphechloral; amphetamine; benzphetamine; chlorphentermine; clobenzorex; cloforex; clominorex; clortermine; cyclexedrine; dextroamphetamine; diphemethoxidine, N-ethylamphetamine; fenbutrazate; fenisorex; fenproporex; fludorex; fluminorex; furfurylmethylamphetamine; levamfetamine; levophacetoperane; mefenorex; metamfepramone; methamphetamine; norpseudoephedrine; pentorex; phendimetrazine; phenmetrazine; piclorex; phytopharm 57; zonisamide, neuromedin U and analogs or derivatives thereof, oxyntomodulin and analogs or derivatives thereof, Neurokinin-1 receptor antagonists (NK-1 antagonists); and Qnexa.

The compounds of the invention may be used in form of a pharmaceutical composition. Thus, in another aspect, the present invention provides a pharmaceutical composition comprising at least one compound of the invention (or a pharmaceutically acceptable salt thereof) and a pharmaceutically acceptable carrier and optionally at least one further therapeutically active agent as defined above. The term "pharmaceutically acceptable salts" refers to salts prepared from pharmaceutically acceptable non-toxic bases or acids including inorganic bases or acids and organic bases or acids as defined hereinabove.

Conveniently, the compounds of the invention may be combined in intimate admixture with a pharmaceutical carrier according to conventional pharmaceutical techniques. The carrier may take a wide variety of forms depending on the form of preparation desired for administration (as defined hereinafter).

The compounds of the invention are ROR (gamma) receptor ligands and have been shown to be useful in the treatment, control or prevention of diseases, disorders or conditions responsive to the modulation of the ROR (gamma) receptor, e.g. diabetes and diabetes-related disorders, in particular type II diabetes.

Therefore, the present invention provides in a further aspect a method for the treatment or prevention of disorders, diseases or conditions responsive to the modulation of the ROR gamma receptor in a subject in need thereof, which comprises administering to the subject a therapeutically or prophylactically effective amount of at least one compound of the invention, or a pharmaceutically acceptable salt thereof, optionally in combination with at least one further therapeutically active agent as defined above.

More specifically, the present invention provides a method for the treatment or prevention of diabetes and diabetes-related disorders in a subject in need thereof which comprises administering to said subject a therapeutically or prophylactically effective amount of at least one ROR gamma receptor ligand of the present invention, optionally in combination with at least one further therapeutically active agent as defined above.

In particular, the present invention provides a method for the treatment or prevention of type II diabetes in a subject in need thereof which comprises administering to the subject a therapeutically or prophylactically effective amount of at least one compound of the invention, or a pharmaceutically acceptable salt thereof, optionally in combination with at least one further therapeutically active agent as defined above.

The terms "administration of" or "administering" a compound of the invention should be understood to mean providing a compound of the invention (or a prodrug of a compound of the invention) or a pharmaceutical composition thereof to a subject in need of treatment. The administration of the compounds of the present invention in order to practice the present methods of therapy is carried out by administering a therapeutically or prophylactically effective amount of the compound (or composition) of the invention and optionally a therapeutically effective amount of at least one further therapeutically active compound to a subject in need of such treatment or prophylaxis.

The term "therapeutically effective amount" as used herein means the amount of a compound of the invention that will elicit the desired biological or medical response in a tissue, system, or subject, which includes alleviation of the symptoms of the disorder being treated. The term "prophylactically effective amount" as used herein means the amount of a compound of the invention that will elicit the desired biological or medical response in a tissue, system, or subject to prevent the onset of the disorder in subjects as risk for the disorder. The therapeutically or prophylactically effective amount, or dosage, of a specific compound of the invention is determined by the physician, but depends on factors such as the exact disease to be treated, the severity of the disease and other diseases or conditions from which the patient suffers, the chosen route of administration, other drugs and treatments which the patient may concomitantly require, the patients age and constitution and other factors in the physician's judgment.

Any suitable route of administration may be employed for providing a subject, especially a human with a therapeutically effective dosage of a compound of the present invention. For example, oral, rectal, topical, parenteral (e.g. subcutaneous or intravenous infusion, and subcutaneous or intravenous injection), ocular, pulmonary, nasal, and the like may be employed. Dosage forms include tablets, troches, dispersions, suspensions, solutions, capsules, creams, ointments, aerosols, and the like. Preferably compounds of the invention are administered orally or parenterally.

The effective dosage of active ingredient employed may vary depending on the particular compound of choice, the mode of administration, the condition being treated and the severity of the condition being treated. Such dosage may be ascertained readily by a person skilled in the art.

Typically a compound or the invention (or combinations thereof) are administered at a daily dosage of from about 0.001 mg to about 50 mgs per kilogram of subject body weight, preferably given in a single dose or in divided doses two to six times a day, or in sustained release form. For example, in the case of a 70 kg adult human, the total daily dose will generally be from about 0.07 mgs to about 3500 mgs. This dosage regimen may be adjusted to provide the optimal therapeutic response. In case of oral administration, a suitable dosage range is, e.g. from about 0.01 mg to about 1500 mg of one or more compounds of the invention per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 600, 750, 1000, 1250 or 1500 mgs of the active ingredient for the symptomatic adjustment of the dosage to the patient to be treated. In case of intranasal administration, a suitable dosage range is e.g. a formulation comprising 0.001-10 percent by weight solutions or suspensions of one or more compounds of the invention may be used. In case of intravenous administration, a suitable dosage range is from about 0.001 mg to about 50 mg, preferably from 0.01 mg to about 50 mg, more preferably 0.1 mg to 10 mg, of one or more compounds of the invention per kg of body weight per day.

The above dosage regimen may be adjusted to provide the optimal therapeutic response. It may be necessary to use dosages outside these limits in some cases. The exact amount of prophylactic or therapeutic dosage of one or more compounds of the invention will, of course, vary depending on the particular compound or compounds of choice, the mode of administration, the condition being treated and the severity of the condition being treated. It will also vary according to the age, weight and response of the individual patient. Such dosage may be ascertained readily by a person skilled in the art.

As indicated above, the present invention also contemplates the use of compounds of the present invention in combination with at least one further therapeutically active compound. Such further therapeutically active compound may be administered, by a route and in an amount commonly used therefore, and may be administered separately or combined (in single or separate pharmaceutical compositions), simultaneously or sequentially with one or more compounds of the invention. In case of simultaneous use, a pharmaceutical composition comprising both the at least one compound of the invention and the at least one additional therapeutically active agent may be used. Accordingly, the present invention also refers to administration of a single pharmaceutical dosage formulation comprising at least one ROR gamma receptor ligand in combination with at least one further therapeutically active agent, as well as administration of each active agent in its own separate pharmaceutical dosage formulation. Where separate dosage formulations are used, the individual components of the composition can be administered at essentially the same time, i.e., concurrently, or sequentially, i.e. prior to or subsequent to the administration of the other component of the composition. It is understood that the present invention includes all such regimes of simultaneous or sequential treatment, and the terms "administration" and "administering" are to be interpreted accordingly.

Various organic or inorganic carrier materials conventionally used as materials for pharmaceutical preparations may be used as pharmaceutically acceptable carrier for the compounds of the invention and the route of administration chosen. They are blended as excipient, lubricant, binder or disintegrant for solid preparations; and solvent, solubilizing agent, suspending agent, isotonicity agent, buffer, soothing agent and the like for liquid preparations. Where necessary, an additive for pharmaceutical preparations such as preservative, antioxidant, colorant, sweetening agent and the like can be used.

Typical examples of an excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate, magnesium aluminate metasilicate and the like. Typical examples of a lubricant include magnesium stearate, calcium stearate, talc, colloidal silica and the like. Typical examples of a binder include pregelatinized starch, saccharose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropyl methylcellulose, polyvinylpyrrolidone and the like. Typical examples of a disintegrant include lactose, sucrose, starch, carboxymethylcellulose, calcium carboxymethylcellulose, sodium croscarmellose, sodium carboxymethyl starch, light anhydrous silicic acid, low-substituted hydroxypropylcellulose and the like. Typical examples of a solvent include water for injection, physiological saline, Ringer's solution, alcohol, propylene glycol, polyethylene glycol, sesame oil, corn oil, olive oil, cottonseed oil and the like. Typical examples of a solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like. Typical examples of a suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil; and the like. Typical examples of an isotonicity agent include sodium chloride, glycerol, D-mannitol, D-sorbitol, glucose and the like. Typical examples of a buffer include phosphate buffer, acetate buffer, carbonate buffer, citrate buffer and the like. Typical examples of a soothing agent include benzyl alcohol and the like. Typical examples of a preservative include p-oxybenzoates, chlorobutanol, benzyl alcohol, phenethyl alcohol, dehydroacetic acid, sorbic acid and the like. Typical examples of an antioxidant include sulfite, ascorbate and the like. Typical examples of a colorant include aqueous edible tar pigments (e.g., foodcolors such as Food Color Red Nos. 2 and 3, Food Color Yellow Nos. 4 and 5, Food Color Blue Nos. 1 and 2 etc.), water insoluble lake pigments (e.g., aluminum salt of the aforementioned aqueous edible tar pigment), natural pigments (e.g., beta carotene, chlorophyll, red iron oxide and yellow ferric oxide) and the like. Typical examples of a sweetening agent include saccharin sodium, dipotassium glycyrrhizinate, aspartame, stevia and the like.

Examples of a suitable dosage form for a compound of the present invention include oral preparations such as tablet (including sugar-coated tablet, film-coated tablet, sublingual tablet, orally disintegrating tablet), capsule (including soft capsule, microcapsule), granule, powder, troche, syrup, emulsion, suspension, film (e.g., mouth cavity disintegrating film) and the like; or parenteral preparations such as injections (e.g., subcutaneous injections, intravenous injections, intramuscular injections and intraperitoneal injections), external agents (e.g., preparations for nasal administration, transdermal preparations and ointments), suppositories (e.g., rectal suppositories and vaginal suppositories), pellets, drops, eye drops, pulmonary preparations (inhalations) and the like. In addition, these preparations may be sustained-release preparations (e.g., sustained-release microcapsule), such as an immediate release preparation or a sustained-release preparation.

The pharmaceutical compositions of the invention may be produced according to a method conventionally used in the field of pharmaceutical preparations. The content of the at least one compound of the invention in a pharmaceutical composition varies depending on the nature of the compound, the route of administration (and thus the nature of the pharmaceutical preparation), etc., and is e.g. from 1 to 90 wt %, preferably from 5 to 80 wt %.

In a further aspect the present invention also relates to a kit providing a pharmaceutical composition of the invention comprising at least one compound of the invention and optionally at least one further therapeutically active compound. In one embodiment, the kit, according to this invention, may comprise a single oral dosage formulation comprising both at least one ROR (gamma) receptor ligand and at least one further therapeutically active ingredient in one compartment of the kit. In another embodiment, the kit, according to this invention, may comprise at least two separate pharmaceutical compositions in separate compartments, which are a first unit dosage form comprising a prophylactically or therapeutically effective amount of at least one ROR (gamma) receptor ligand, or a pharmaceutically acceptable salt or ester thereof, and a pharmaceutically acceptable carrier or diluents in a first compartment, and a second unit dosage form comprising a prophylactically or therapeutically effective amount of at least one further active ingredient, or a pharmaceutically acceptable salt or ester thereof, and a pharmaceutically acceptable carrier or diluent in a second compartment.

The present invention is further exemplified by the following specific examples, which are intended to illustrate the invention and are not to be construed as limiting the scope of the invention in any manner. It is understood that a skilled person in the art can readily prepare additional compounds of the present invention based on the procedures described herein. Those skilled in the art will readily understand that known variations of the conditions and processes of the following preparative procedures can be used to prepare these compounds.

EXAMPLES

Materials and Methods

All chemicals and solvents were purchased from ABCR, Acros, Aldrich, J. T. Baker, Fluka, Merck, TCI, or Lancaster and used as such with the following exceptions: THF and DMF were dried by passage over two 4"×36" columns of anhydrous neutral A-2 alumina (Macherey and Nagel; activated over night at 300° C. under a flow of $N_2$) under an atmosphere of argon ($H_2O$ content<30 ppm, Karl-Fischer titration). All temperatures are degrees Celsius unless otherwise noted. All non-aqueous reactions were performed in flame dried glassware under an atmosphere of argon/nitrogen unless stated otherwise. TLC was performed on Merck silica gel 60 F254 TLC aluminum plates and visualized with UV fluorescence quenching and p-Anysaldehyde-stain. Concentrations under reduced pressure were performed by rotary evaporation at 37° C. at the appropriated pressure, unless otherwise noted. Column chromatographic purification was performed as flash chromatography with 0.3-0.5 bar pressure on silica gel (60 Å, 40-64 µm). Distilled technical grade solvents were employed. The yields given refer to the purified products. Uncorrected melting points were measured on a Büchi B-540 melting point apparatus using open glass capillaries. NMR data was recorded on a VARIAN Mercury 300 MHz, Gemini 300 MHz, Bruker ARX 300, Bruker AV 400, Bruker DRX 400 spectrometer. Measurements were carried out at RT (ca. 22° C.) unless otherwise noted. Chemical shifts are given in ppm with the residual solvent signal as internal standard [d]-chloroform at 7.26 and 77.00 ppm, $d_6$-DMSO at 2.50 and 39.52 ppm, [d]-methanol at 3.31 and 49.00 ppm, for $^1H$— and $^{13}C$, respectively. Multiplicities are abbreviated as follows: singlet (s), doublet (d), triplet (t), apparent triplet (at), doublet-doublet (dd), triplet-doublet (td), doublet-doublet-doublet (ddd), and multiplet (m), coupling constant(s) are given in Hz. $^{13}C$-NMR spectra were recorded with 1H-decoupling. Infrared spectra were recorded on a Perkin Elmer RXI FT-IR Spectrophotometer as thin films, absorptions are given in wavenumbers ($cm^{-1}$). Mass spectrometric analyses were performed by the mass spectrometry service of the Laboratorium für Organische Chemie at ETH Zürich by L. Bertschi and O. Greter under direction of Dr. Zhang. ESI and HRMS measurements were carried out on a Bruker Daltonics maxis and Varian IonSpec ESI FT-ICR at 4.7 Tesla. EI measurements were carried out on a Waters Micromass AutoSpec Ultima at 70 eV.

The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., Protective Groups in Organic Synthesis, John Wiley and Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Luciferase activity assay. Typically, 3T3L1 cells were grown to 60-70% confluence in a 24 well dish and transfected with the reporter genes (pMMP3-pGL3) (0.05 µg), pCMV-Renilla as internal reference (0.05 µg) and the expression vectors for RORgamma (0.1 µg) by use of the transfection reagent Fugene according to manufacture's protocol (Invitrogen). Cells were grown for an additional 48 h after transfection. Luciferase activity was measured using the Luciferase Detection System following manufacture's protocol (Promega).

Insulin tolerance test. Typically, C57B6 mice (age 6 weeks) were fed a high fat diet (60% calories derived from fat, Kliba) supplemented with 1β,3α,7α,12α-tetrahydroxy-5β-cholan-24-oate (or tetraol compound) at 0.1% or 0.01% or cholic acid (or CA) at 0.1% and 0.01%. High fat diet feeding alone served as a control. After 6 weeks mice were tested for insulin sensitivity by injection of 0.5 U/kg insulin, i.p. Blood glucose concentrations were measured before injection and at 30, 60, 90 and 120 min post injection. Relative drop in blood glucose was calculated for each mouse by dividing the time point value by the starting blood glucose value.

Therapeutic efficacy Typically, C57B6 mice (age 6 weeks) were fed a high fat diet (60% calories derived from fat, Kliba) for 6 week to induce obesity related insulin resistance. Subsequently the mice were divided in three groups: the first one was continued on high fat diet supplemented with 0.01% tetraol compound, the second one on high fat diet supplemented with 0.01% cholic acid and the last one on high fat diet as a control. After 6 and 12 weeks on the respective diets, blood glucose was measured using an Contour glucose monitor (Bayer AG, Diabetes Care, Switzerland) and circulating insulin concentrations were determined using the rat/mouse insulin assay supplied by Meso Scale Discovery (Gaithersburg, Md., USA).

Example 1: Synthesis of methyl-1β,3α,7α,12α-tetrahydroxy-5β-cholan-24-oate

(a) Methyl 3-oxo,7α,12α-dihydroxy-5β-cholan-24-oate

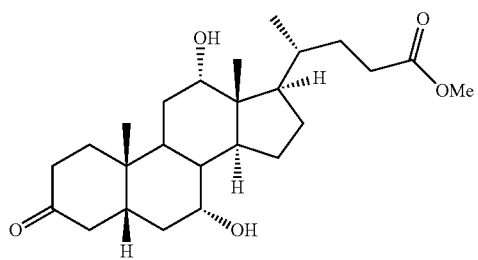 [SMILES: COC(=O)CC[C@@H](C)[C@H]1CC[C@H]2C3C(C[C@H](O)[C@]12C)[C@@]1(C)CCC(=O)C[C@H]1C[C@H]3O]

Cholic acid (50 g, 0.12 mol) was converted into the corresponding methylester (51 g, 98%) according to literature procedures (Rohacova J., et al. Org. Biomol. Chem., 2009, 7, 4973-4980; Tohma M. et al., Chem. Pharm. Bull. 1986, 34 (7), 2890-2899). To a solution of the obtained methylester (23 g, 59 mmol) in toluene (400 mL), Ag$_2$CO$_3$/CELITE® diatomaceous earth (40 g) was added. The mixture was heated at 150° C. under vigorous stirring until TLC showed complete conversion of the starting material (Rf=0.27, AcOEt 100%) into a single less polar product (Rf=0.58, AcOEt 100%). After 9 h, the mixture was allowed to cool down to r.t. and the solid precipitates were removed by filtration through a pad of CELITE® diatomaceous earth. The solvent was removed under reduced pressure to give the crude material, which was triturated with Et$_2$O to give the corresponding ketone-diol (19.7 g, 87%) as a white solid. Analytical data were in full agreement with the reported values (Rohacova J., et al. Org. Biomol. Chem., 2009, 7, 4973-4980; Tohma M. et al., Chem. Pharm. Bull. 1986, 34 (7), 2890-2899).

(b) Methyl 3-oxo,7α,12α-diacetoxy-5β-cholan-24-oate

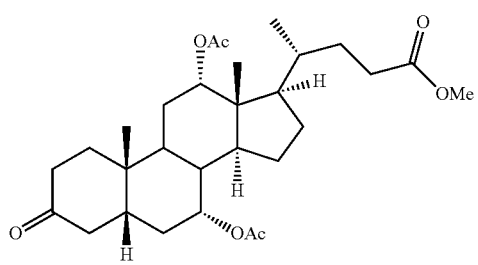 [SMILES: COC(=O)CC[C@@H](C)[C@H]1CC[C@H]2C3C(C[C@H](OC(C)=O)[C@]12C)[C@@]1(C)CCC(=O)C[C@H]1C[C@H]3OC(C)=O]

To a solution of ketone-diol of step (a) (13 g, 31 mmol) in a mixture of acetic anhydride and pyridine (50% vol, 100 mL), DMAP (380 mg, 3.1 mmol) was added. The reaction mixture was stirred for 1 h at r.t., cooled at 0° C. and quenched by adding MeOH dropwise. The solvents were concentrated under reduced pressure and the residue was dissolved in EtOAc and washed with 1M HCl and NaHCO$_3$ $_{(aq.)}$. The organic phase was concentrated under reduced pressure to give a solid residue, which was recrystallized from EtOAc/hexanes to afford bis acetoxy sterol (14.8 g, 95%), whose analytical data were in full agreement with the reported values (Tohma M. et al., Chem. Pharm. Bull. 1986, 34 (7), 2890-2899).

(c) Methyl 7α,12α-diacetoxy-2β,4β-dibromo-3-oxo-5β-cholan-24-oate

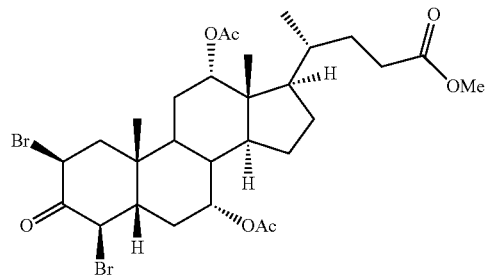 [SMILES: COC(=O)CC[C@@H](C)[C@H]1CC[C@H]2C3C(C[C@H](OC(C)=O)[C@]12C)[C@@]1(C)C[C@H](Br)C(=O)[C@H](Br)[C@H]1C[C@H]3OC(C)=O]

The bis acetoxy ketone of step (b) (11.47 g, 23 mmol) was dissolved in a mixture of CHCl$_3$ (20 mL) and acetic acid (40 mL). A solution of Br$_2$ (2.34 mL, 46 mmol) in acetic acid (24 mL) was added dropwise. After 1 h stirring at r.t., the mixture was quenched with NaHSO$_{3(aq)}$ and concentrated under reduced pressure to ¼ of its volume. The residue was dissolved in EtOAc and washed with NaHCO$_3$(aq). The organic phase was concentrated under reduced pressure and the residue was triturated with diisopropylether to afford 2,4-dibromo derivative (13.49 g, 90%) as 85:15 mixture of two major epimers, suitable however to be used as such in the next steps. An aliquot of the crude was crystallized twice from CH$_2$CL$_2$/Et$_2$O to give pure 2,4 dibromo derivative (M.P.=196° C., Lit$^2$=196-98° C.), whose analytical and spectroscopic data were identical to the ones described (Tohma M. et al., Chem. Pharm. Bull. 1986, 34 (7), 2890-2899).

(d) Methyl 7α,12α-diacetoxy-3-oxo-5β-chol-1-en-24-oate

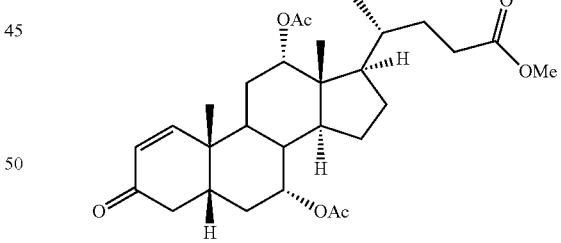

To a solution of the dibromoketone of step (c) (10.6 g, 16 mmol) in DMF (85 mL) were added Li$_2$CO$_3$ (1.9 g, 24 mmol) and LiBr (2.1 g, 24 mmol). After stirring at 80° C. under nitrogen for 8 h, TLC showed complete conversion of the starting material (Rf=0.53, Hexanes/EtOAc 80:20) into a single more polar spot (Rf=0.35, Hexanes/EtOAc 80:20). The mixture was diluted with EtOAc and washed with 1 M HCl. The organic phase was concentrated under reduced pressure to give a crude residue which was triturated with diisopropylether to afford the intermediate Methyl 7α,12α-diacetoxy-4β-bromo-3-oxo-5β-chol-1-en-24-oate as a white solid (8.6 g, 92%), which was reacted in the next step without further purification.

To a solution of the previously obtained ¹Δ-4-Bromo-enone in acetic acid (80 mL), finely divided Zn powder (4 g, 63 mmol) was added. After stirring for 30 min. at r.t., complete conversion of the starting material into a single spot was observed on TLC (Rf=0.54, Hexanes/EtOAc, 70:30). The solids were filtered through a pad of CELITE® diatomaceous earth and the resulting solution was concentrated under reduced pressure to ⅕ of its volume. The residue was then added into a flask containing 500 mL of ice-cold distilled water to give a solid precipitate, which was filtered off and purified by flash chromatography (Hexanes/EtOAc, 70:30) to afford the desired enone (5.6 g, 76%), whose analytical data were in full agreement with the reported ones (Tohma M. et al., Chem. Pharm. Bull. 1986, 34 (7), 2890-2899).

(e) Methyl 1β-dimethylphenylsilyl-7α,12α-diacetoxy-3-oxo-5β-cholan-24-oate

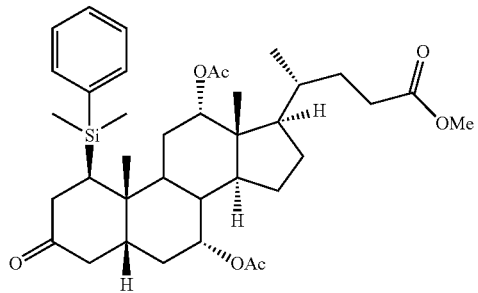 [SMILES: COC(=O)CC[C@@H](C)[C@H]1CC[C@H]2C3C(C[C@H](OC(C)=O)[C@]12C)[C@]1(C)[C@@H](CC(=O)C[C@H]1[Si](C)(C)c1ccccc1)C[C@H]3OC(C)=O]

Lithium metal (418 mg, 59.7 mmol) was suspended in THF (20 mL), cooled at 0° C., and Phenyldimethylchlorosilane (4.34 ml, 26.3 mmol) was added. Stirring was continued for 1 h at 0° C., then the resulting red-purple solution was transferred via cannula to a suspension of CuI (2.5 g, 13.1 mmol) in THF (20 mL), previously cooled at −30° C. After 30 minutes, a solution of Methyl 7α,12α-diacetoxy-3-oxo-5β-chol-1-en-24-oate of step (d) (6 g, 11.9 mmol) in THF (20 mL) was added dropwise. After 30 minutes stirring at −30° C., the reaction was quenched by adding 0.1 M HCl and the mixture was extracted with Et₂O. Evaporation of the solvents under reduced pressure afforded an oily residue, which was purified by flash chromatography to give the silyl ketone. White solid: m. p.=162° C.; [α]$_D^{20}$; =+44.9 (c=1.00 in CHCl₃); ¹H NMR (400 MHz, CDCl₃): δ 7.47-7.43 (m, 2H), 7.36-7.32 (m, 3H), 5.12 (at, J=2.7 Hz, 1H), 4.93 (dd, J=5.6, 3.4 Hz, 1H), 3.65 (s, 3H), 2.99 (dd, J=15.6, 12.7 Hz, 1H), 2.44 (dd, J=14.8, 7.5 Hz, 1H), 2.34 (ddd, J=15.3, 10.0, 5.2 Hz, 1H), 2.32-2.15 (m, 3H), 2.10 (s, 3H), 2.05 (s, 3H), 2.00-1.75 (m, 6H), 1.75-1.60 (m, 3H), 1.60-1.47 (m, 3H), 1.44-1.24 (m, 4H), 1.15-1.04 (m, 1H), 0.99 (s, 3H), 0.81 (d, J=6.4 Hz, 3H), 0.71 (s, 3H), 0.38 (s, 3H), 0.33 (s, 3H); ¹³C NMR (101 MHz, CDCl₃): δ 212.2, 174.4, 170.5, 170.1, 139.3, 133.8, 133.8, 129.0, 127.9, 127.9, 75.2, 70.3, 51.5, 47.3, 45.0, 44.5, 43.5, 40.3, 38.4, 38.2, 37.5, 34.6, 32.3, 30.9, 30.7, 30.7, 30.5, 27.2, 25.8, 22.7, 22.1, 21.5, 21.3, 17.5, 12.2, −0.3, −0.4.; IR (film): ν=2949, 2870, 1734, 1435, 1425, 1376, 1240, 1110, 1024 cm⁻¹; HRMS (ES⁺): m/z: Calcd for C₃₇H₅₄O₇NaSi (M⁺+Na): 661.3531, found: 661.3525.

(f) Methyl 1β,3α-dihydroxy-7α,12α-diacetoxy-5β-cholan-24-oate

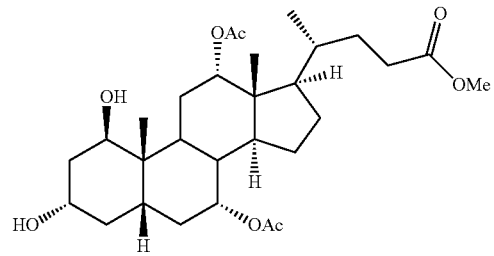 [SMILES: COC(=O)CC[C@@H](C)[C@H]1CC[C@H]2C3C(C[C@H](OC(C)=O)[C@]12C)[C@]1(C)[C@@H](C[C@H](O)C[C@H]1O)C[C@H]3OC(C)=O]

To a solution of the silyl-ketone of step (e) (2.5 g, 3.91 mmol) in a mixture of peracetic acid (20 mL, 40% in acetic acid) and acetic acid (10 mL), Hg(OAc)₂ (1.5 g, 4.70 mmol) was added. The mixture was stirred at r.t. for 6 h, cooled at 0° C. and carefully quenched by slow addition of NaHSO₃ (40% aq). The reaction mixture was concentrated under reduced pressure, diluted with AcOEt and washed with NaHCO₃ and brine. The solvents were evaporated under reduced pressure to give the crude intermediate hydroxyketone as a major product (Rf=0.29, hexanes/EtOAc 4:3) which was reacted in the next step without purification.

The crude material was dissolved in a mixture of CH₂Cl₂/THF (1:2, 45 mL) and added to a previously prepared solution of Na(OAc)₃BH at 0° C., obtained by adding NaBH₄ (296 mg, 7.8 mmol) to a mixture of acetic acid/THF (1:1, 10 mL). After stirring at 0° C. for 30 min., complete conversion of the starting material into a major product (Rf=0.25, EtOAc 100%) was observed, without any detectable amount of the corresponding 3β epimer (Rf=0.48, EtOAc 100%). The solvents were evaporated under reduced pressure and the residue was dissolved in AcOEt and washed with brine. Evaporation of the solvents under reduced pressure and purification of the residue by flash chromatography (EtOAc/isopropanol 10:1) gave pure diol (860 mg, 42%), whose analytical and spectroscopic data were in full agreement with the reported ones (Tohma M. et al., Chem. Pharm. Bull. 1986, 34 (7), 2890-2899).

(g) Methyl-1β,3α,7α,12α-tetrahydroxy-5β-cholan-24-oate

Selective hydrolysis of the acetate groups using anhydrous base (such as sodium methoxide in methanol) yields the tetrahydroxy-methylester. The identity of the compound was confirmed through methylation of the corresponding free acid 1β,3α,7α,12α-tetrahydroxy-5β-cholan-24-oic acid. Free acid (7 mg, 0.016 mmol) was added to a mixture of MeOH (1 mL) containing acetyl chloride (1 μL, 0.19 mmol). The mixture was stirred for 4 h at r.t., the solvents were evaporated to afford the desired methylester (5 mg, 69%). ¹H NMR (300 MHz, CD₃OD): δ 3.93 (at, J=2.8, 1H), 3.90-3.82 (m, 2H), 3.80 (dd, J=5.0, 2.3 Hz, 1H), 3.65 (s, 3H), 2.45-2.28 (m, 4H), 2.01 (dd, J=12.0, 4.8 Hz, 1H), 1.92-1.48 (m, 12H), 1.47-1.24 (m, 7H), 1.19-1.02 (m, 2H), 1.01 (s, 3H), 1.00 (d, J=6.2 Hz, 3H), 0.72 (s, 3H).

Example 2: Synthesis of isopropyl-1β,3α,7α,12α-tetrahydroxy-5β-cholan-24-oate

(a) Methyl 3α,7α,12α-triacetoxy-5β-cholan-24-oate

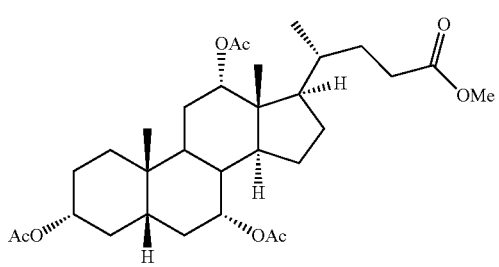 [SMILES: COC(=O)CC[C@@H](C)[C@H]1CC[C@H]2C3C(C[C@H](OC(C)=O)[C@]12C)[C@@]1(C)CC[C@@H](OC(C)=O)C[C@H]1C[C@H]3OC(C)=O]

Cholic acid (50 g, 0.12 mol) was converted into the corresponding methylester as reported in Example 1(a). To a solution of the obtained methylester (30 g, 71 mmol) in a mixture of acetic anhydride and pyridine (50% vol, 156 mL), DMAP (860 mg, 7.1 mmol) was added. The reaction mixture was stirred for 1 h at r.t., cooled at 0° C., quenched by adding MeOH (60 mL) dropwise and concentrated almost to dryness. The residue was dissolved in EtOAc and washed with 1M HCl and NaHCO$_3$ (aq.). The organic phase was concentrated under reduced pressure to give the corresponding triacetoxy sterol (39 g, 100%), whose analytical properties were identical a s reported in the literature (Opsenica D. et al, J. Med. Chem. 2000, 43, 3274-3282).

(b) Isopropyl 3α-hydroxy,7α,12α-diacetoxy-5β-cholan-24-oate

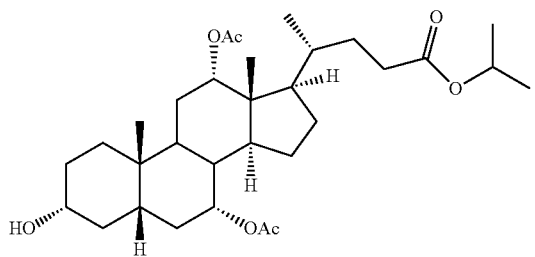 [SMILES: CC(=O)O[C@H]1CC2C([C@H](OC(C)=O)C[C@@H]3C[C@H](O)CC[C@]23C)[C@@H]2CC[C@H]([C@H](C)CCC(=O)OC(C)C)[C@@]12C]

To a solution of the sterol of step (a) (29.5 g, 54 mmol) in isopropanol (150 mL) was added a previously prepared solution of sodium isopropoxide, obtained by dissolving finely divided Na (2.5 g, 108 mmol) in isopropanol (240 mL). The mixture was stirred at r.t. for 20 minutes, and then quenched by adding KHSO$_4$ (sat. aq.). The solvent was removed under reduced pressure to give the crude material, which was re-dissolved in EtOAc and washed with brine. Evaporation of the solvent and trituration of the crude residue with diisopropyl ether, gave the corresponding alcohol (28.7 g, 100%). $^1$H NMR (400 MHz, CDCl$_3$): δ 5.09-5.07 (m, 1H), 4.99 (sept., J=6.3 Hz, 1H), 4.90 (dd, J=5.5, 2.9 Hz, 1H), 3.54-3.45 (m, 1H), 2.29 (ddd, J=15.6, 10.3, 5.1 Hz, 1H), 2.18 (dd, J=9.4, 6.9 Hz, 1H), 2.12 (s, 3H), 2.08 (s, 3H), 2.07-1.81 (m, 7H), 1.81-1.49 (m, 8H), 1.49-1.24 (m, 6H), 1.22 (d, J=6.3 Hz, 6H), 1.17-0.95 (m, 2H), 0.90 (s, 3H), 0.81 (d, J=6.8 Hz, 3H), 0.72 (s, 3H).

(c) Isopropyl 3-oxo,7α,12α-diacetoxy-5β-cholan-24-oate

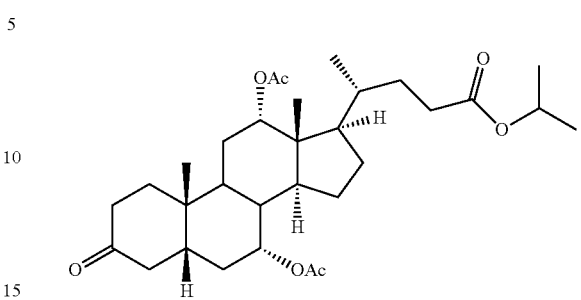

To a solution of the alcohol of step (b) (28.7 g, 54 mmol) in acetic acid (550 mL), a solution of NaClO (218 mL, 5% (aq), 268 mmol) was added dropwise. The reaction mixture was stirred for 1 h at r.t., quenched with NaHSO$_3$ (sat. aq), and the solvent was concentrated under reduced pressure. The residue was dissolved in EtOAc and washed with NaHCO$_3$ (aq.) and brine. The solvent was evaporated under reduced pressure to give a solid residue, which was purified by flash chromatography (Hexanes/EtOAc 4:3) to afford the desired ketone (21.6 g, 76%). $^1$H NMR (400 MHz, CDCl$_3$): δ 5.11 (at, J=2.7 Hz, 1H), 5.04-4.95 (m, 2H), 2.98 (dd, J=15.6, 13.9 Hz, 1H), 2.29 (ddd, J=15.6, 6.9, 5.3 Hz, 1H), 2.23-2.07 (m, 6H), 2.11 (s, 3H), 2.06 (s, 3H), 1.99-1.74 (m, 5H), 1.74-1.57 (m, 4H), 1.49-1.24 (m, 6H), 1.22 (d, J=6.3 Hz, 6H), 1.19-1.07 (m, 1H), 1.01 (s, 3H), 0.82 (d, J=6.5 Hz, 3H), 0.76 (s, 3H).

(d) Isopropyl 7α,12α-diacetoxy-2β,4β-dibromo-3-oxo-5β-cholan-24-oate

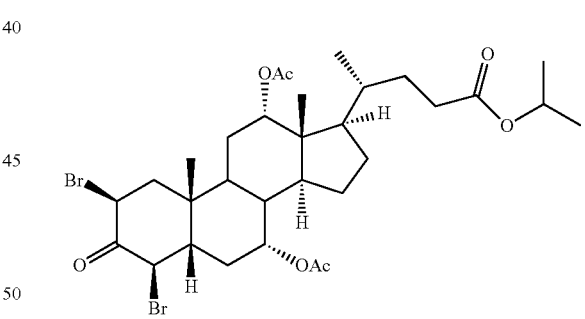

To the ketone of step (c) (10 g, 18.8 mmol) was dissolved in acetic acid (120 mL). A solution of Br$_2$ (1.93 mL, 37.5 mmol) in acetic acid (100 mL) was added dropwise. After 1 h stirring at r.t., the mixture was poured into water. The solid precipitated was filtered, dried, and triturated with diisopropyl ether to afford the 2,4-dibromo derivative (9.2 g, 71%). $^1$H NMR (400 MHz, CDCl$_3$): δ 5.35 (d, J=11.9 Hz, 1H), 5.18 (at, J=2.7 Hz, 1H), 5.06 (dd, J=6.0, 3.1 Hz, 1H), 4.99 (sept., J=6.3 Hz, 1H), 4.65 (dd, J=14.2, 4.9 Hz, 1H), 2.62 (dd, J=14.2, 5.5 Hz, 1H), 2.54 (dat, J=15.7, 2.0 Hz, 1H), 2.30 (ddd, J=14.9, 9.4, 5.6 Hz, 1H), 2.21-2.10 (m, 2H), 2.13 (s, 3H), 2.12 (s, 3H), 2.04-1.81 (m, 4H), 1.80-1.62 (m, 6H), 1.50-1.24 (m, 4H), 1.21 (d, J=5.7 Hz, 6H), 1.18-1.12 (m, 1H), 1.01 (s, 3H), 0.82 (d, J=6.4 Hz, 3H), 0.76 (s, 3H).

(e) Isopropyl 7α,12α-diacetoxy-4β-bromo-3-oxo-5β-chol-1-en-24-oate

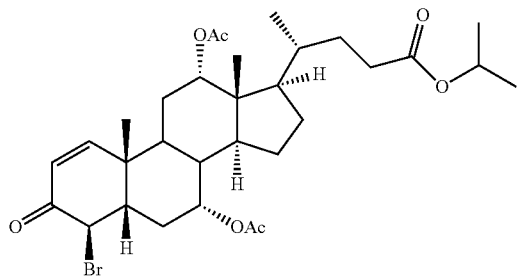 [SMILES: CC(=O)O[C@H]1CC2C([C@H](OC(C)=O)C[C@@H]3[C@@H](Br)C(=O)C=C[C@]23C)[C@@H]2CC[C@H]([C@H](C)CCC(=O)OC(C)C)[C@@]12C]

To a solution of the dibromoketone of step (d) (9.2 g, 13.3 mmol) in DMF (60 mL) were added Li$_2$CO$_3$ (1.6 g, 20 mmol) and LiBr (1.7 g, 20 mmol). After stirring at 80° C. under nitrogen for 8 h, the mixture was poured into water and the solid precipitate was filtered, dried and triturated with diisopropyl ether to afford the desired enone (6.8 g, 84%). $^1$H NMR (400 MHz, CDCl$_3$): δ 6.77 (d, J=10.3 Hz, 1H), 6.05 (d, J=10.3 Hz, 1H), 5.34 (d, J=13.4 Hz, 1H), 5.09-5.06 (m, 2H), 4.99 (sept., J=6.2 Hz, 1H), 2.62 (dat, J=16.0, 2.0 Hz, 1H), 2.29 (ddd, J=15.3, 9.6, 5.7 Hz, 1H), 2.24-2.10 (m, 2H), 2.13 (s, 3H), 2.08 (s, 3H), 2.06-1.95 (m, 1H), 1.94-1.74 (m, 6H), 1.73-1.62 (m, 2H), 1.52-1.29 (m, 4H), 1.26 (s, 3H), 1.22 (d, J=6.1 Hz, 6H), 1.18-1.11 (m, 1H), 0.80 (d, J=6.5 Hz, 3H), 0.78 (s, 3H).

(f) Isopropyl 1-epoxy-7α,12α-diacetoxy-4β-bromo-5β-cholan-24-oate

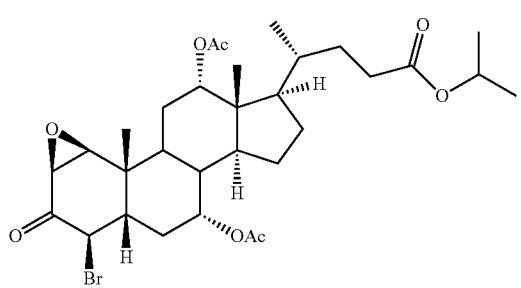 [SMILES: CC(=O)O[C@H]1CC2C([C@H](OC(C)=O)C[C@@H]3[C@@H](Br)C(=O)[C@H]4O[C@H]4[C@]23C)[C@@H]2CC[C@H]([C@H](C)CCC(=O)OC(C)C)[C@@]12C]

To a solution of the bromo-enone of step (e) (6.8 g, 11.2 mmol) in Ethanol (450 mL) containing DBU (1.83 mL, 12.3 mmol), urea-H$_2$O$_2$ complex (2.6 g, 27.6 mmol) was added in three portions over a period of 5 h, while stirring at r.t. The mixture was quenched with NaHSO$_3$ (aq.) and KHSO$_4$ (aq.) and the solvents were concentrated under reduced pressure. The residue was dissolved in EtOAc and washed with 1M HCl and brine. Evaporation of the solvent under reduced pressure and purification of the crude by flash chromatography (Hexanes/EtOAc 4:2) gave the desired epoxide (4.2 g, 60%). $^1$H NMR (400 MHz, CDCl$_3$): δ 5.09 (at, J=2.9 Hz, 1H), 5.06-5.04 (m, 1H), 4.99 (sept., J=6.4 Hz, 1H), 4.74 (d, J=11.1 Hz, 1H), 3.50 (d, J=3.6 Hz, 1H), 3.42 (d, J=3.6 Hz, 1H), 2.45-2.25 (m, 3H), 2.18 (dd, J=9.2, 6.9 Hz, 1H), 2.11 (s, 3H), 2.10 (s, 3H), 1.94-1.61 (m, 8H), 1.49-1.35 (m, 3H), 1.34 (s, 3H), 1.32-1.24 (m, 3H), 1.22 (d, J=6.4 Hz, 6H), 0.80 (d, J=6.5 Hz, 3H), 0.76 (s, 3H).

(g) Isopropyl 1β-hydroxy-2α,4β-dibromo-7α,12α-diacetoxy-3-oxo-5β-cholan-24-oate

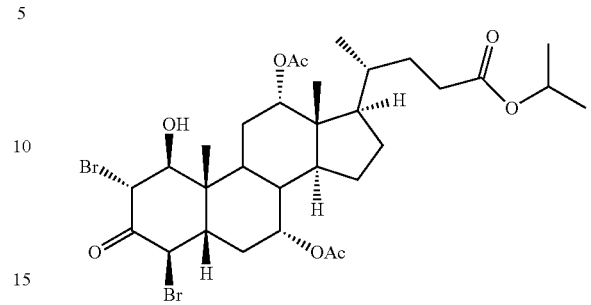

To a solution of the epoxide of step (f) (300 mg, 0.48 mmol) in acetic acid (7 mL), LiBr (104 mg, 1.2 mmol) was added. After stirring at r.t. for 30 minutes the reaction mixture was poured into water and the white precipitate was filtered and dried to give the corresponding hydroxyketone (283 mg, 86%). $^1$H NMR (400 MHz, CDCl$_3$): δ 5.68 (d, J=13.3 Hz, 1H), 5.10 (at, J=2.8 Hz, 1H), 5.05 (dd, J=5.6, 2.7 Hz, 1H), 4.99 (sept., J=6.0 Hz, 1H), 4.48 (d, J=4.6 Hz, 1H), 4.13 (at, J=4.5 Hz, 1H), 2.72 (td, J=11.7, 3.9 Hz, 1H), 2.61 (dat, J=15.6, 2.6 Hz, 1H), 2.45 (d, J=4.0 Hz, 1H), 2.38 (ddd, J=12.8, 5.2, 2.2 Hz, 1H), 2.29 (ddd, J=15.2, 9.6, 5.2 Hz, 1H), 2.18 (dd, J=9.2, 7.0 Hz, 1H), 2.16-2.09 (m, 2H), 2.15 (s, 3H), 2.03 (s, 3H), 1.95-1.66 (m, 6H), 1.51-1.25 (m, 4H), 1.22 (s, 3H), 1.22 (d, J=6.4 Hz, 6H), 1.15 (m, 1H), 0.80 (d, J=6.5 Hz, 3H), 0.78 (s, 3H).

(h) Isopropyl 1β,3α-dihydroxy-2α,4β-dibromo-7α,12α-diacetoxy-5β-cholan-24-oate

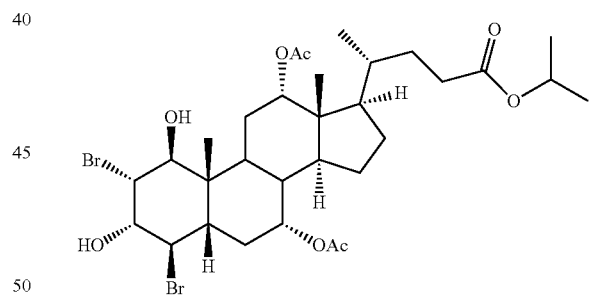

To a solution of the epoxide of step (f) (420 mg, 0.67 mmol) in acetic acid (10 mL), LiBr (117 mg, 1.3 mmol) was added. To the reaction mixture, a previously prepared solution of sodium triacetoxyborohydride in acetic acid (obtained by adding 30.5 mg of NaBH$_4$ to 2 mL of acetic acid at 0° C.), was added. After stirring at r.t. for 30 minutes the solvent was evaporated and the residue was dissolved in EtOAc and washed with brine. Evaporation of the solvent and trituration of the crude with diisopropyl ether gave the dibromo-diol derivative (402 mg, 85%). $^1$H NMR (400 MHz, CDCl$_3$): δ 5.04 (at, J=2.4 Hz, 1H), 4.98 (sept., J=6.5 Hz, 1H), 5.00-4.95 (m, 1H), 4.84 (at, J=11.1 Hz, 1H), 4.56 (dd, J=4.2, 3.1 Hz, 1H), 4.19 (br, 1H), 4.06 (dat, J=10.4, 4.4 Hz, 1H), 2.79 (d, J=4.5 Hz, 1H), 2.29 (ddd, J=15.2, 9.9, 5.5 Hz, 1H), 2.20-2.05 (m, 3H), 2.15 (s, 3H), 2.02 (s, 3H), 1.95-1.82

(m, 2H), 1.81-1.62 (m, 5H), 1.53-1.25 (m, 5H), 1.21 (d, J=6.3 Hz, 6H), 1.16-1.12 (m, 1H) 1.14 (s, 3H), 0.79 (d, J=6.5 Hz, 3H), 0.75 (s, 3H).

(i) Isopropyl 1β-hydroxy-7α,12α-diacetoxy-3-keto-5β-cholan-24-oate

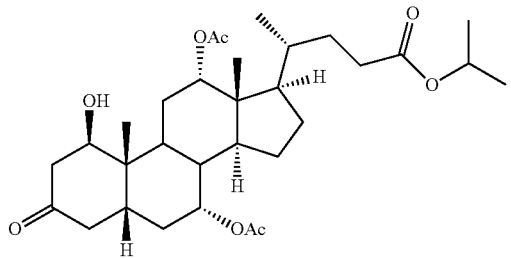 [SMILES: CC(=O)O[C@H]1CC2C([C@H](OC(C)=O)C[C@@H]3CC(=O)C[C@@H](O)[C@]23C)[C@@H]2CC[C@H]([C@H](C)CCC(=O)OC(C)C)[C@@]12C]

The dibromoketone of step (g) (100 mg, 0.14 mmol) was dissolved in THF (5 mL) and hydrogenated at ambient temperature and pressure over 5% Pd/C (15.0 mg) in the presence of sodium acetate (38 mg, 0.425 mmol) for 5 h. The catalyst was filtered through a pad of CELITE® diatomaceous earth and the solvent evaporated under reduced pressure, the residue was purified by flash chromatography (Hexanes/EtOAc 40:60) to afford the hydroxyketone (35 mg, 45%). $^1$H NMR (400 MHz, CDCl$_3$): δ 5.11 (at, J=2.4 Hz, 1H), 5.03-5.00 (m, 1H), 4.99 (sept., J=6.3 Hz, 1H), 4.09-4.04 (m, 1H), 2.98 (dd, J=15.5, 13.0, 1H), 2.54 (dd, J=14.8, 2.0 Hz, 1H), 2.39-2.29 (m, 3H), 2.22-2.04 (m, 2H), 2.11 (s, 3H), 2.07 (s, 3H), 1.94-1.64 (m, 10H), 1.48-1.24 (m, 6H), 1.22 (d, J=6.3 Hz, 6H), 1.14 (s, 3H), 0.82 (d, J=6.5 Hz, 3H), 0.77 (s, 3H).

(j) Isopropyl 1β,3α-dihydroxy-7α,12α-diacetoxy-5β-cholan-24-oate

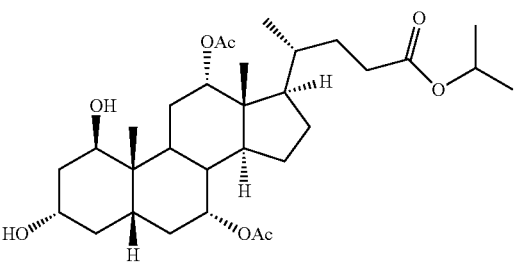 [SMILES: CC(=O)O[C@H]1CC2C([C@H](OC(C)=O)C[C@@H]3C[C@H](O)C[C@@H](O)[C@]23C)[C@@H]2CC[C@H]([C@H](C)CCC(=O)OC(C)C)[C@@]12C]

Dibromo-diol of step (h) (50 mg, 0.71 mmol) in Ethanol (30 mL) containing NaOAc (11.5 mg, 0.14 mmol) and acetic acid (30 µL) was hydrogenated over Raney Nickel (8 mg) at 180 atm and r.t. for 72 h. Filtration of the catalyst over a pad of CELITE® diatomaceous earth, evaporation of the solvents under reduced pressure and purification of the crude by silica gel flash chromatography (AcOEt 100%) gave the desired diol (18 mg, 46%). $^1$H NMR (400 MHz, CDCl$_3$): δ 5.06 (at, J=2.5 Hz, 1H), 4.99 (sept., J=6.3 Hz, 1H), 4.92-4.89 (m, 1H), 4.06-3.98 (m, 1H), 3.88-3.85 (m, 1H) 2.29 (ddd, J=15.5, 9.6, 5.6, 1H), 2.18 (dd, J=9.5, 6.8 Hz, 1H), 2.13 (s, 3H), 2.09 (s, 3H), 1.96-1.73 (m, 8H), 1.73-1.36 (m, 13H), 1.22 (d, J=6.3 Hz, 6H), 1.17-1.07 (m, 1H), 1.03 (s, 3H), 0.80 (d, J=6.5 Hz, 3H), 0.77 (s, 3H).

In analogy to Example 1(g), selective hydrolysis of the acetate groups using anhydrous base (such as sodium isopropoxide in isopropanol) yields the tetrahydroxy-isopropylester.

Example 3: Synthesis of isopropyl-1β,3α-dihydroxy-2α-bromo-7α,12α-diacetoxy-5β-cholan-24-oate (a) Isopropyl 1-epoxy-7α,12α-diacetoxy-5β-cholan-24-oate

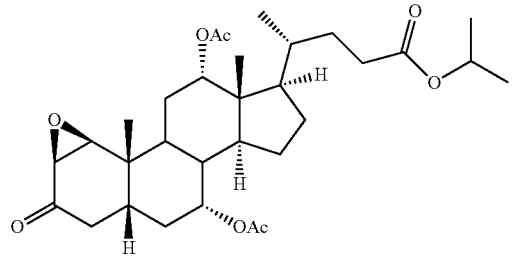 [SMILES: CC(=O)O[C@H]1CC2C([C@H](OC(C)=O)C[C@@H]3CC(=O)[C@H]4O[C@H]4[C@]23C)[C@@H]2CC[C@H]([C@H](C)CCC(=O)OC(C)C)[C@@]12C]

The bromide obtained in Example 2(f) (200 mg, 0.32 mmol) in THF (5 mL) containing NaOAc (52 mg, 0.64 mmol) was hydrogenated over Raney Nickel (20 mg) at ambient temperature and pressure for 30 minutes. The catalyst was filtered over a pad of CELITE® diatomaceous earth, the solvent was evaporated under reduced pressure and the residue was dissolved in EtOAc and washed with brine. The organic extracts were evaporated under reduced pressure and the crude residue was triturated with diisopropyl ether to give the epoxyketone (141 mg, 81%). $^1$H NMR (400 MHz, CDCl$_3$): δ 5.10-5.08 (br, 1H), 5.03-4.96 (m, 2H), 3.34 (d, J=3.8 Hz, 1H), 3.27 (d, J=3.8 Hz, 1H), 2.70 (dd, J=19.3, 11.9 Hz, 1H), 2.34-2.25 (m, 2H), 2.20-2.06 (m, 2H), 2.11 (s, 3H), 2.07 (s, 3H), 1.92-1.73 (m, 7H), 1.71-1.60 (m, 4H), 1.47-1.34 (m, 2H), 1.29 (s, 3H), 1.21 (d, J=6.3 Hz, 6H), 1.34-1.25 (m, 2H), 0.81 (d, J=6.5 Hz, 3H), 0.76 (s, 3H).

(b) Isopropyl 1β-hydroxy-2α-bromo-7α,12α-diacetoxy-3-oxo-5β-cholan-24-oate

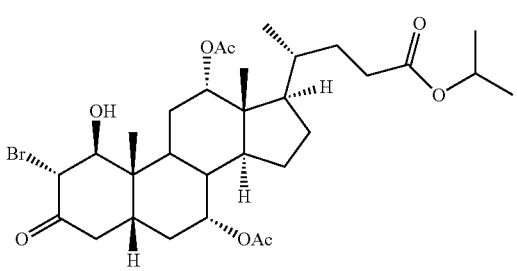 [SMILES: CC(=O)O[C@H]1CC2C([C@H](OC(C)=O)C[C@@H]3CC(=O)[C@H](Br)[C@@H](O)[C@]23C)[C@@H]2CC[C@H]([C@H](C)CCC(=O)OC(C)C)[C@@]12C]

To a solution of the epoxyketone obtained in step (a) (30 mg, 0.05 mmol) in acetic acid (0.7 mL), LiBr (9.53 mg, 0.1 mmol) was added. After stirring at r.t. for 30 minutes the reaction mixture was poured into water and NaHCO$_3$ was added until neutral pH. The mixture was then extracted with EtOAc and the solvents removed under reduced pressure to give the hydroxyketone (33 mg, 96%). $^1$H NMR (400 MHz, CDCl$_3$): δ 5.13-5.10 (br, 1H), 5.03-4.93 (m, 2H), 4.54 (d, J=8.1 Hz, 1H), 3.82 (dd, J=7.7 Hz, 1H), 3.20 (dd, J=16.4, 13.5 Hz, 1H), 2.38-2.12 (m, 7H), 2.10 (s, 3H), 2.09 (s, 3H), 1.96-1.61 (m, 8H), 1.41-1.23 (m, 5H), 1.22 (d, J=6.2 Hz, 6H), 1.15 (s, 3H), 0.80 (d, J=6.5 Hz, 3H), 0.78 (s, 3H).

(c) Isopropyl 1β,3α-dihydroxy-2α-bromo-7α,12α-diacetoxy-5β-cholan-24-oate

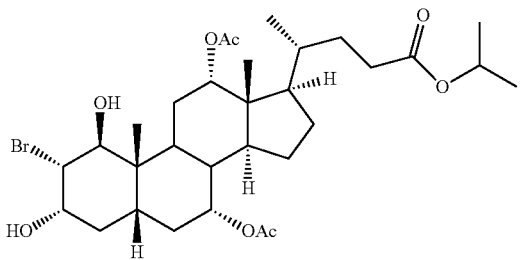 [SMILES: CC(=O)O[C@H]1CC2C([C@H](OC(C)=O)C[C@@H]3C[C@H](O)[C@H](Br)[C@@H](O)[C@]23C)[C@@H]2CC[C@H]([C@H](C)CCC(=O)OC(C)C)[C@@]12C]

To a solution of the epoxyketone obtained in step (a) (50 mg, 0.091 mmol) in acetic acid (1 mL), LiBr (16 mg, 0.18 mmol) was added. To the reaction mixture, a previously prepared solution of sodium triacetoxyborohydride in acetic acid (obtained by adding 4.1 mg of NaBH$_4$ to 0.5 mL of acetic acid at 0° C.), was added. After stirring at r.t. for 30 minutes the reaction mixture was concentrated under reduced pressure and the residue was dissolved in EtOAc and washed with brine, the solvent was evaporated under reduced pressure to give the product (43 mg, 75%). $^1$H NMR (400 MHz, CDCl$_3$): δ 5.05 (at, J=2.6 Hz, 1H), 4.99 (sept., J=6.2 Hz, 1H), 4.94-4.87 (m, 1H), 4.53-4.49 (m, 1H), 4.15-4.09 (m, 1H), 3.94-3.85 (m, 1H), 2.34-2.10 (m, 6H), 2.10 (s, 3H), 2.04 (s, 3H), 1.94-1.54 (m, 10H), 1.54-1.24 (m, 5H), 1.22 (d, J=6.2 Hz, 6H), 1.16-1.07 (m, 1H), 1.05 (s, 3H), 0.80 (d, J=6.4 Hz, 3H), 0.74 (s, 3H).

Subsequent reduction yields the corresponding diol compound, which can be converted to the tetrahydroxy-ester or free acid through partial or full hydrolysis, respectively.

Example 4: Synthesis of 1β,3α,7α,12α-tetrahydroxy-5β-cholan-24-oic acid

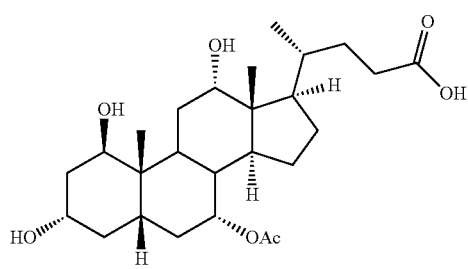 [SMILES: CC(=O)O[C@@H]1C[C@@H]2C[C@H](O)C[C@@H](O)[C@]2(C)C2C[C@H](O)[C@]3(C)[C@@H]([C@H](C)CCC(=O)O)CC[C@H]3C21]

The diol obtained in step 1(f) (1.5 g, 2.87 mmol) was added to a mixture of MeOH/H$_2$O (3:2, 50 mL) containing NaOH (1.5 g, 28.7 mmol). The mixture was heated at 120° C. and, after 13 h, TLC showed the presence of a single more polar spot (Rf=0.48, CHCl$_3$/MeOH/CH$_3$COOH 5:1:0.5). The reaction mixture was allowed to cool at r.t., and the base excess was neutralized by adding cationic exchange resin DOWEX® 50WX2, 50-100, until neutral/slightly acidic pH. The resin was filtered off, washed with H$_2$O/MeOH (50:50) and the solvent was removed under reduced pressure to give the desired free acid-tetraol (1.1 g, 90%). White solid: m. p.=288-290° C., Lit (Tohma M. et al., Chem. Pharm. Bull. 1986, 34 (7), 2890-2899)=288-290° C. [α]$_D^{20}$; =+19.6 (c=0.33 in MeOH); $^1$H NMR (400 MHz, d6-DMSO): δ 3.76 (at, J=2.8 Hz, 1H), 3.72-3.62 (m, 1H), 3.62-3.57 (m, 2H), 2.30-2.16 (m, 2H), 2.14-2.04 (m, 2H), 2.01-1.92 (m, 1H), 1.81-1.57 (m, 7H), 1.49-1.11 (m, 9H), 1.01-0.92 (m, 1H), 0.91 (d, J=6.4 Hz, 3H), 0.86 (s, 3H), 0.58 (s 3H); $^{13}$C NMR (101 MHz, d6-DMSO): δ 175.0, 71.4, 70.9, 66.1, 64.7, 46.1, 45.5, 41.3, 39.9, 39.2, 38.7, 37.6, 35.2, 35.1, 34.6, 31.0, 30.9, 28.6, 27.7, 27.2, 22.9, 17.3, 16.9, 12.4; IR (film): ν=3370, 2922, 2858, 2359, 2342, 1705, 1377, 1184, 1027, 1033 cm$^{-1}$; HRMS (ES$^+$): m/z: Calcd for C$_{24}$H$_{39}$O$_6$ (M$^-$–H): 423.2752, found: 423.2734.

Alternatively, the diol-diacetate-isopropylester obtained in step 2(j) (20 mg, 0.036 mmol) can be hydrolyzed under the same conditions reported above to furnish the free acid-tetraol (13 mg, 84%), whose analytical data where superimposable to the ones of the compound obtained above.

Example 5: Synthesis of methyl 3α-hydroxy-7α,12α-diacetoxy-5β-chol-1-en-24-oate

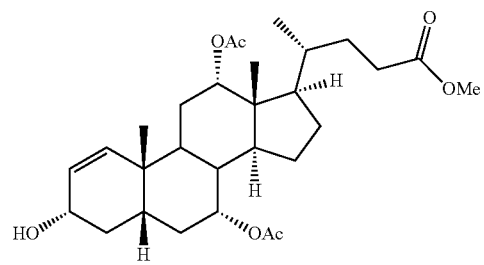 [SMILES: COC(=O)CC[C@@H](C)[C@H]1CC[C@H]2C3C(C[C@H](OC(C)=O)[C@]12C)[C@@]1(C)C=C[C@@H](O)C[C@H]1C[C@H]3OC(C)=O]

A suspension of the enone of Example 1(d) (250 mg, 0.49 mmol) and CeCl$_3$ (278 mg, 0.75 mmol) in MeOH (8 mL) was cooled at –78° C. and NaBH$_4$ (28 mg, 0.75 mmol) was added. After stirring at –78° C. for 30 minutes, the reaction mixture was quenched with acetone (0.5 mL) and the solvent was evaporated under reduced pressure. The residue was diluted with EtOAc and washed with brine. The organic phase was concentrated under reduced pressure to give the crude material which was triturated with diisopropyl ether to give the desired allylic alcohol (244 mg, 97%). $^1$H NMR (400 MHz, CDCl$_3$): δ 5.55 (s, 2H), 5.06 (at, J=2.8 Hz, 1H), 4.91 (dd, J=5.9, 3.1 Hz, 1H), 4.26-4.18 (m, 1H), 3.65 (s, 3H), 2.34 (ddd, J=15.9, 10.6, 5.1 Hz, 1H), 2.22 (dd, J=9.6, 6.9 Hz, 1H), 2.10 (s, 3H), 2.08 (s, 3H), 2.01-1.54 (m, 11H), 1.53-1.22 (m, 6H), 1.15-1.03 (m, 1H), 1.00 (s, 3H), 0.79 (d, J=6.3 Hz, 3H), 0.73 (s, 3H).

Example 6: Synthesis of methyl-1β-epoxy-3α-hydroxy-7α,12α-diacetoxy-5β-cholan-24-oate and methyl-1α-epoxy-3α-hydroxy-7α,12α-diacetoxy-5β-cholan-24-oate

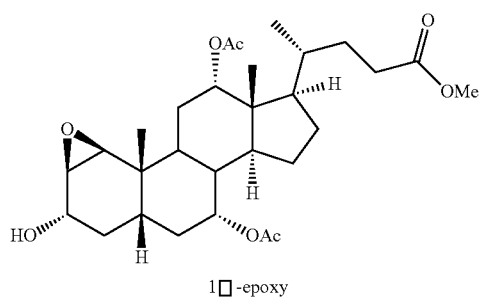

1□-epoxy

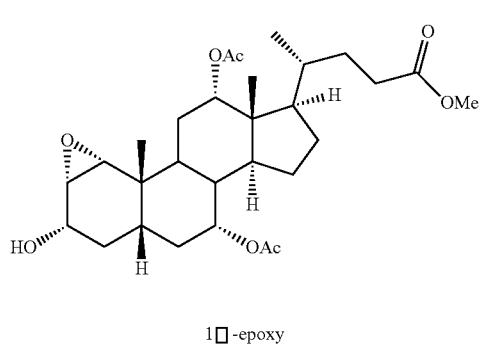

1□-epoxy

The allylic alcohol obtained in example 4 (100 mg, 0.39 mmol) was dissolved in a mixture of THF (3 mL) and water (1 mL), and NBS (89 mg, 0.39 mmol) was added. The mixture was stirred at r.t. for 24 h, after which time complete conversion of the starting material into two spots on TLC corresponding to an epimeric mixture of epoxides could be observed (Hexane/EtOAc 3:4, Rf=0.38 and Rf=0.42, respectively). The mixture was quenched with $NaHSO_3$ and extracted with EtOAc. Evaporation of the solvent afforded the crude residue which was purified by flash chromatography (Hexanes/EtOAc 3:4) to give the 1□-epoxide (31 mg, 30%): $^1$H NMR (400 MHz, $CDCl_3$): δ 5.08 (at, J=2.9, 1H), 4.86 (dd, J=5.8, 2.9 Hz, 1H), 3.88 (dd, J=10.8, 6.3 Hz, 1H), 3.65 (s, 3H), 3.14 (brd, J=3.6 Hz, 1H), 3.05 (brd, J=3.6 Hz, 1H), 2.34 (ddd, J=15.4, 10.0, 4.7 Hz, 1H), 2.22 (dd, J=9.9, 7.0 Hz, 1H), 2.15 (s, 3H), 2.06 (s, 3H), 1.98-1.54 (m, 12H), 1.53-1.18 (m, 6H), 1.18-1.02 (m, 1H), 1.12 (s, 3H), 0.79 (d, J=6.3 Hz, 3H), 0.75 (s, 3H).

Further elution afforded the epimeric 1□-epoxide (29 mg, 28%): $^1$H NMR (400 MHz, $CDCl_3$): δ 5.09 (at, J=2.8, 1H), 4.85 (dd, J=6.3, 3.6 Hz, 1H), 3.88 (dd, J=10.8, 6.3 Hz, 1H), 3.66 (s, 3H), 3.32 (brd, J=4.1 Hz, 1H), 2.93 (d, J=4.1 Hz, 1H), 2.35 (ddd, J=15.5, 10.3, 5.6 Hz, 1H), 2.21 (dd, J=8.9, 2.6 Hz, 1H), 2.14 (s, 3H), 2.06 (s, 3H), 1.98-1.54 (m, 12H), 1.53-1.18 (m, 7H), 1.07 (s, 3H), 0.82 (d, J=6.3 Hz, 3H), 0.75 (s, 3H).

Example 6: Synthesis of 1β,3β,7α,12α-tetrahydroxy-5β-cholan-24-oic acid (a) Methyl 1β,3β-dihydroxy-7α,12α-diacetoxy-5β-cholan-24-oate

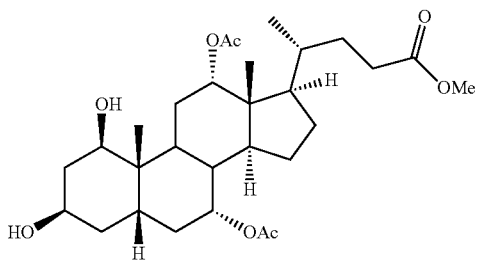 [SMILES: COC(=O)CC[C@@H](C)[C@H]1CC[C@H]2C3C(C[C@H](OC(C)=O)[C@]12C)[C@]1(C)[C@@H](C[C@@H](O)C[C@H]1O)C[C@H]3OC(C)=O]

Hydroxyketone obtained according to Tohma M. et al, Chem. Pharm. Bull. 1986, 34 (7), 2890-2899 (100 mg, 0.19 mmol) was reduced in the presence of $NaBH_4$ (7.5 mg, 0.19 mmol) in THF (4 mL) at r.t. After 10 minutes the solvent was evaporated under reduced pressure and the residue was diluted with EtOAc and washed with brine to afford the crude material consisting of two spots on TLC in about 1:1 ratio corresponding to the desired 3β epimer (Rf=0.48, EtOAc 100%) and the 3α epimer (Rf=0.25, EtOAc 100%). Purification by flash chromatography (Hexanes/EtOAc 40:60) afforded the desired 3β-diol (40 mg, 39.8%). $^1$H NMR (400 MHz, $CDCl_3$): δ 5.07 (at, J=2.8, 1H), 4.94 (dd, J=6.3, 3.6 Hz, 1H), 4.17-4.13 (m, 1H), 3.78-3.74 (m, 1H), 3.66 (s, 3H), 2.40-2.14 (m, 2H), 2.10 (s, 3H), 2.08 (s, 3H), 2.03-1.64 (m, 8H), 1.63-1.54 (m, 6H), 1.53-1.23 (m, 4H), 1.18-1.00 (m, 2H), 1.11 (s, 3H), 0.81 (d, J=6.3 Hz, 3H), 0.75 (s, 3H).

(b) 1β,3β,7α,12α-tetrahydroxy-5β-cholan-24-oic acid

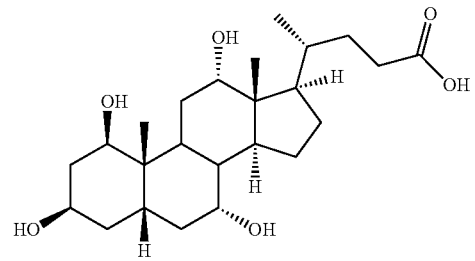 [SMILES: C[C@H](CCC(=O)O)[C@H]1CC[C@H]2C3C(C[C@H](O)[C@]12C)[C@]1(C)[C@@H](C[C@@H](O)C[C@H]1O)C[C@H]3O]

The 3β-diol obtained in step (a) (40 mg, 0.077 mmol) was added to a mixture of MeOH/$H_2O$ (3:2, 3 mL) containing NaOH (31 mg, 0.77 mmol). The mixture was heated at 120° C. and, after 13 h it was cooled to r.t., and the base excess was neutralized by adding cationic exchange resin DOWEX® 50WX2, 50-100, until neutral/slightly acidic pH. The resin was filtered off, washed with $H_2O$/MeOH (50:50) and the solvent was removed under reduced pressure to give the desired 1β,3β-tetraol (27 mg, 83%). $^1$H NMR (300 MHz, $CD_3OD$): δ 4.06 (at, J=2.8, 1H), 3.94 (at, J=2.4 Hz, 1H), 3.82 (dd, J=6.0, 3.2 Hz, 1H), 3.73-3.70 (m, 1H), 2.64 (at, J=14.2 Hz, 1H), 2.33 (ddd, J=14.8, 9.9, 4.8 Hz, 1H), 2.20

(dd, J=9.4, 7.0 Hz, 1H), 2.16-1.71 (m, 12H), 1.71-1.22 (m, 6H), 1.19-1.02 (m, 1H), 1.07 (s, 3H), 1.01 (d, J=6.3 Hz, 3H), 0.73 (s, 3H).

Example 7: Repression of ROR Gamma Activity Using a Luciferase Assay

Figure 2:
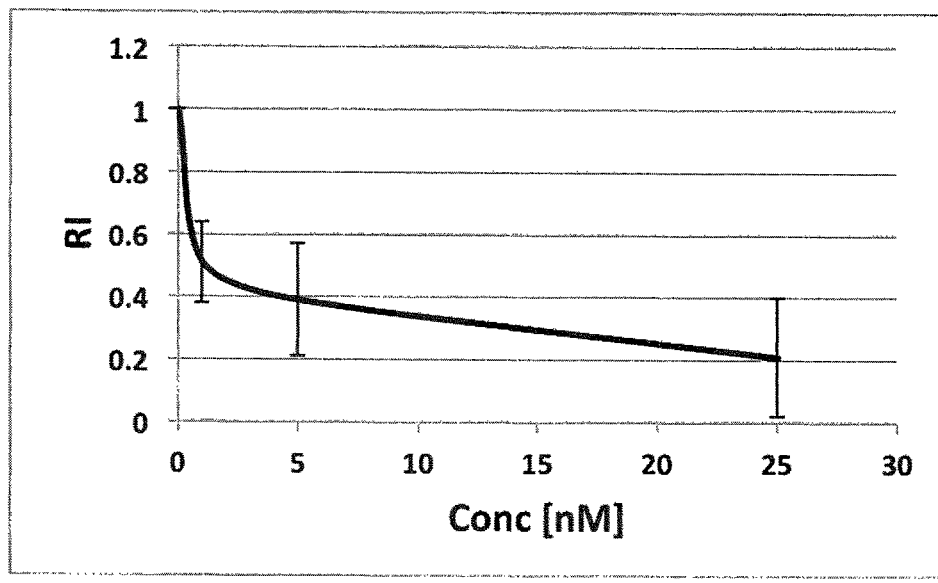
FIG. 2: Inhibition of RORgamma activity (RI=relative inhibition; Conc=concentration of 1β,3α,7α,12α-tetrahydroxy-5β-cholan-24-oate (tetraol) in nM).

1β,3α,7α,12α-Tetrahydroxy-5β-cholan-24-oate (herein also called tetraol or tetraol compound) was tested for its ability to inhibit transcriptional activity of RORγ using a dual luciferase assay (FIG. 1), in which activation of the matrix-metalloproteinase 3 (MMP3) promoter, which is a target gene of RORγ, by RORγ was tested in the presence of different concentrations of compound 1. 3T3L1 Preadipocyte cells were transfected with the reporter gene an expression vector for RORγ as well normalization vector expressing renilla luciferase. Cells were treated after infection with different amounts of RORγ ranging from 1 to 25 nM. Cells were lysed 24 h after treatment with the tetraol compound and firefly as well as renilla luciferase activity was measured. The repression of RORγ activity was calculated from the ratio of firefly over renilla luciferase. Analysis of the tetraol compound in an activity assay shows a dose dependent reduction of RORgamma activity. This is illustrated in FIG. 2, which clearly shows that the relative inhibition (RI, y-axis) is decreasing with increasing concentration of the tetraol compound (conc in nM, x-axis).

Example 8: In Vivo Prevention Efficacy

To test the in vivo efficacy of the tetraol compound mice were fed a high fat diet (60% calories derived from fat) for 6 weeks. The diet was supplemented with 0.1% or 0.01% of the tetraol compound (A and B, respectively, in FIG. 3). Mice receiving high fat diet only (E in FIG. 3) and mice receiving high fat diet supplemented with 0.1% cholic acid (C in FIG. 3) and 0.01% cholic acid (D in FIG. 3), respectively served as control.

Figure 3:
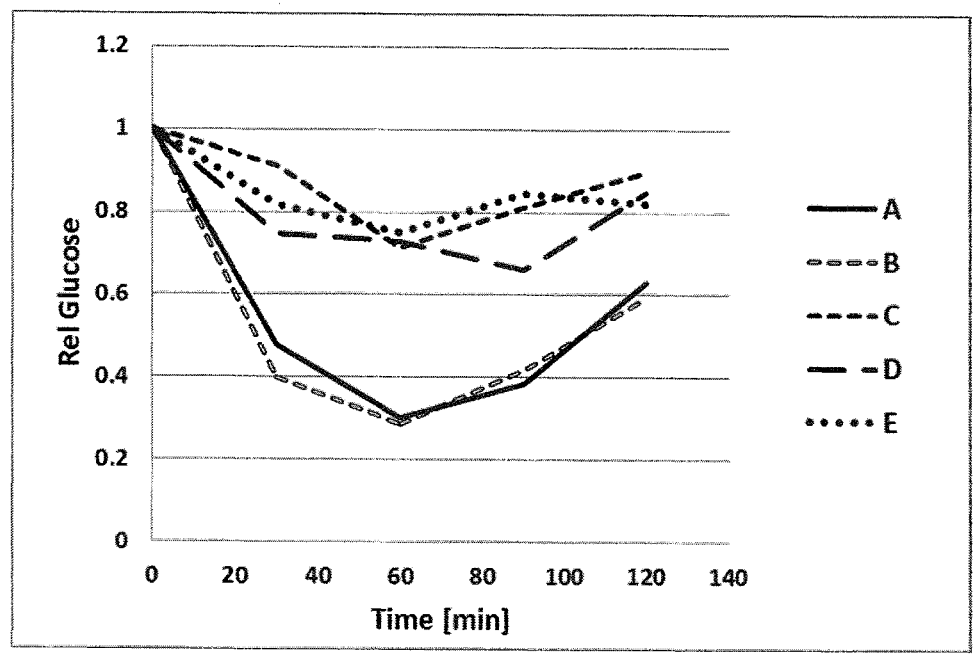
FIG. 3: Effect on insulin sensitivity in mice that were fed a high fat diet in combination with different supplements at different concentrations. The y-axis represents relative glucose levels, the x-axis represents time after insulin injection in min. The high fat diet was given as such (E) or supplemented with tetraol 0.1% (A) or tetraol 0.01% (B) or cholic acid 0.1% (C) or cholic acid 0.01% (D).

FIG. 3 clearly shows, that treatment of mice with the tetraol compound led to a dramatic improvement in insulin sensitivity at either concentration, as measured by an insulin tolerance test.

Example 9: In Vivo Therapeutic Efficacy

To test the in vivo therapeutic efficacy of tetraol compound mice were fed a high fat diet (60% calories derived from fat) for 6 weeks. Afterwards the obese/insulin resistant mice were put on a diet supplemented with either 0.01% of tetraol or 0.01% of cholic acid for either 6 or 12 weeks (0.01% tetraol and 0.01% CA, respectively, in FIGS. 4 and 5).

Figure 4:
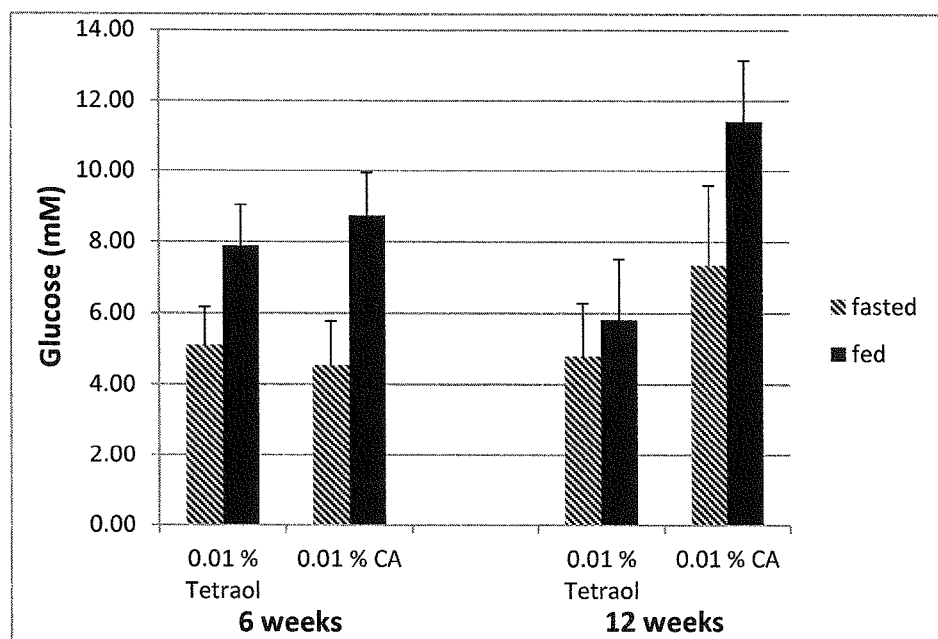
FIG. 4: Effect of tetraol compound and cholic acid as control compound on glucose levels in obese/insulin resistant mice over time (x-axis represents mM glucose, y-axis represents time points of 6 and 12 weeks, striped bars represent fasted mice, filled bars represent fed mice).
Figure 5:
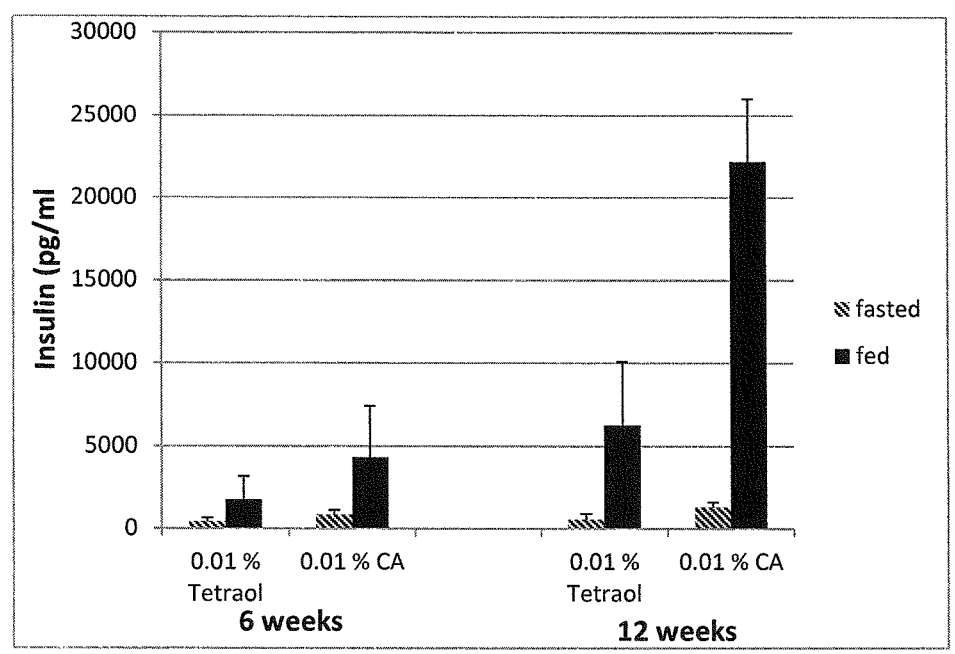
FIG. 5: Effect of tetraol compound and cholic acid as control compound on insulin levels in obese/insulin resistant mice over time (x-axis represents pg/ml Insulin, y-axis represents time points of 6 and 12 weeks, striped bars represent fasted mice, filled bars represent fed mice).

FIGS. 4 and 5 clearly show, that treatment of obese insulin resistant mice with tetraol led over time to a dramatic improvement in insulin sensitivity, as measured by circulating glucose (FIG. 4) and insulin levels (FIG. 5): gluc=glucose levels in mM; ins=insulin levels in pg/ml.

The invention claimed is:

1. Method for the treatment of type II diabetes and type II diabetes-related disorders selected from low glucose tolerance, insulin resistance and hyperglycemia, in a diabetic or prediabetic subject in need thereof which comprises administering to said subject a therapeutically effective amount of at least one compound having a polyhydroxylated cholane skeleton and glycine- and taurine-conjugates thereof of formula V or a pharmaceutically acceptable salt or stereoisomer thereof,

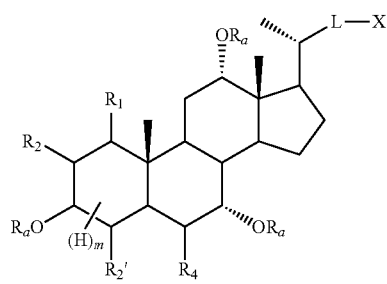

wherein $R_1$ is H, hal, $-OR_a$, $-SR_a$, $-NR_aR_b$, $-COOR_a$, $-CONR_aR_b$, wherein $R_a$ and $R_b$ are independently of each other H or (C1-6)alkyl, or $R_1$ forms together with $R_2$ and the C-atoms to which $R_1$, $R_2$ are linked to an epoxy group;

$R_2$ is H or hal, or $R_2$ forms together with $R_1$ and the C-atoms to which $R_1$, $R_2$ are linked to an epoxy group;

$R_{2'}$ is H or hal, $R_4$ is H, hal, $-OR_a$, $-SR_a$, $-NR_aR_b$, $-COOR_a$, $-CONR_aR_b$, oxo, thio, wherein $R_a$ and $R_b$ are independently of each other H or (C1-6)alkyl, L is a straight-chain C(1-12)alkyl, which is unsubstituted and wherein one or more of the non-adjacent $CH_2$ groups may independently be replaced by a group selected from $-O-$, $-CO-$, $-CO-O-$;

X is H, $-OR_a$, $-COOR_c$, $-CONR_aR_c$, wherein $R_a$ is H or (C1-6)alkyl and $R_c$ is $-H$, $-(C1-6)$alkyl, $-NH-(CH_2)_n-CO_2R_a$ or $-NH-(CH_2)_p-SO_3R_a$, wherein n, p is 1, 2, or 3 and $R_a$ is $-H$ or $-(C1-6)$alkyl, $R_a$ is H or C(1-6)alkyl, m is 0 to 5 and wherein $R_1$ or $R_4$ or both $R_1$ and $R_4$ are $-OR_a$, where $R_a$ is H or (C1-6)alkyl.

2. Method according to claim 1 wherein L is a straight-chain C(1-12)alkyl.

3. Method according to claim 1 wherein X is H, $-OR_a$, $-COOR_c$, $-CONR_aR_c$, wherein $R_a$ is H or (C1-6)alkyl and $R_c$ is $-H$, $-(C1-6)$alkyl, $-NH-CH_2-CO_2R_a$ or $-NH-(CH_2)_2-SO_{3p}R_a$, wherein $R_a$ is $-H$ or $-(C1-6)$alkyl.

4. Method according to claim 1 wherein -L-X is $-(C1-6)$alkyl-COOR$_a$ wherein $R_a$ is $-H$ or $-(C1-6)$alkyl.

5. Method according to claim 1, wherein $R_2$ is H or hal.

6. Method according to claim 1 wherein the compound of formula V is of the formulae Va or Vb

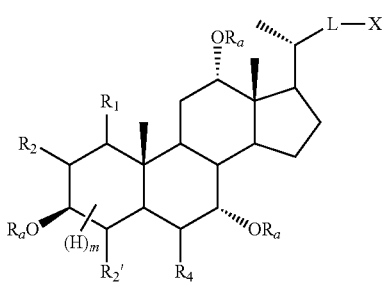

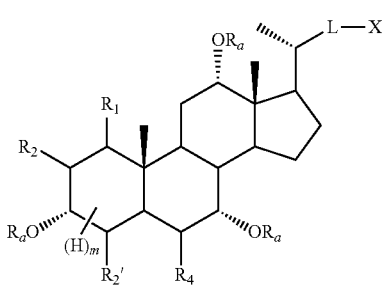

Vb wherein

R₁ is H, hal, —OR_a, —SR_a, —NR_aR_b, —COOR_a, —CONR_aR_b wherein R_a and R_b are independently of each other H or (C1-6)alkyl, or R₁ forms together with R₂ and the C-atoms to which R₁, R₂ are linked to an epoxy group;

R₂ is H or hal, or R₂ forms together with R₁ and the C-atoms to which R₁, R₂ are linked to an epoxy group;

R₂' is H or hal,

R₄ is H, hal, —OR_a, —SR_a, —NR_aR_b, —COOR_a, —CONR_aR_b, oxo, thio wherein R_a and R_b are independently of each other H or (C1-6)alkyl, L is a straight-chain C(1-12)alkyl, which is unsubstituted and wherein one or more of the non-adjacent CH₂ groups may independently be replaced by a group selected from —O—, —CO—, —CO—O;

X is H, —OR_a, —COOR_c, —CONR_aR_c, wherein R_a is H or (C1-6)alkyl and R_c is —H, —(C1-6)alkyl, —NH—(CH₂)_n—CO₂R_a or —NH—(CH₂)_p—SO₃R_a, wherein n, p is 1, 2, or 3 and R_a is or —(C1-6)alkyl, R_a is H or C(1-6)alkyl, m is 0 to 5 and wherein R₁ or R₄ or both R₁ and R₄ are —OR_a, where R_a is H or (C1-6)alkyl.

7. Method according to claim 6 wherein L is a straight-chain C(1-12)alkyl.

8. Method according to claim 6 wherein X is H, —OR_a, —COOR_c, —CONR_aR_c, wherein R_a is H or (C1-6)alkyl and R_c is —H, —(C1-6)alkyl, —NH—CH₂—CO₂R_a or —NH—(CH₂)₂—SO₃pR_a, wherein R_a is —H or —(C1-6)alkyl.

9. Method according to claim 6 wherein -L-X is —(C1-6)alkyl-COOR_a wherein R_a is —H or —(C1-6)alkyl.

10. Method according to claim 1 having formula VIa, VIb and VIc or a pharmaceutically acceptable salt or stereoisomer thereof,

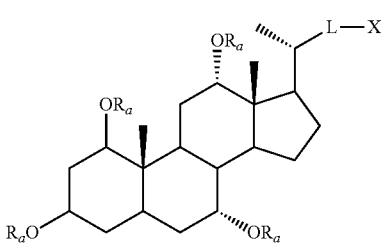

VIb

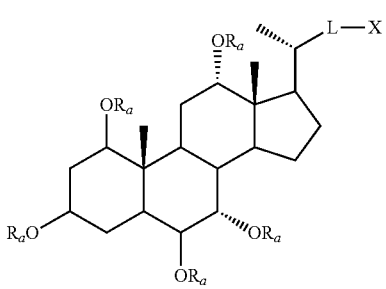

VIc wherein

L is a straight-chain C(1-12)alkyl, which is unsubstituted and wherein one or more of the non-adjacent CH₂ groups may independently be replaced by a group selected from —O—, —CO—, —O—, R_a is H or C(1-6)alkyl, and X is H, —OR_a, —SR_a, —NR_aR_b, —COOR_c, —CONR_aR_c; wherein R_a and R_b are independently of each other H or (C1-6)alkyl and R_c is —H, —(C1-6)alkyl, —NH—(CH₂)_n—CO₂R_a or —NH—(CH₂)_p—SO₃R_a, wherein n, p is 1, 2, or 3 and R_a is —H or —(C1-6) alkyl.

11. Method according to claim 10 wherein L is a straight-chain C(1-12)alkyl.

12. Method according to claim 10 wherein X is H, —OR_a, —COOR_c, —CONR_aR_c, wherein R_a is H or (C1-6)alkyl and R_c is —H, —(C1-6)alkyl, —NH—CH₂—CO₂R_a or —NH—(CH₂)₂—SO₃pR_a, wherein R_a is —H or —(C1-6)alkyl.

13. Method according to claim 10 wherein -L-X is —(C1-6)alkyl-COOR_a wherein R_a is —H or —(C1-6)alkyl.

14. Method according to claim 1 wherein a compound of formula V has the formula VIa₁, VIa₂, VIb₁, VIb₂, VIb₃ and VIb₄

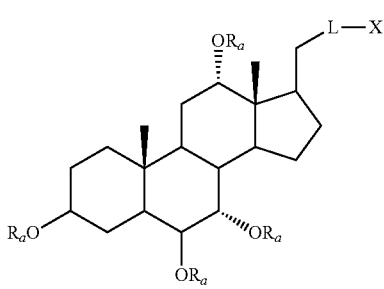

VIa

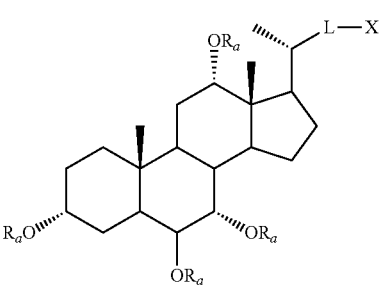

VIa₁

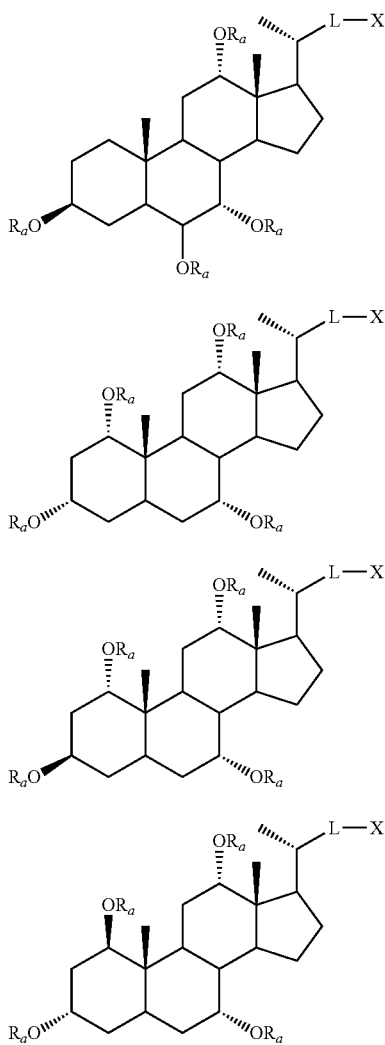

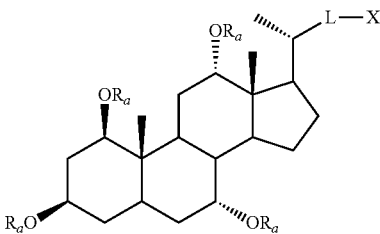

wherein
L is a straight-chain C(1-12)alkyl, which is unsubstituted and wherein one or more of the non-adjacent $CH_2$ groups may independently be replaced by a group selected from —O—, —CO—, —CO—O—,
$R_a$ is H or C(1-6)alkyl, and
X is H, —$OR_a$, —$SR_a$, —$NR_aR_b$, —$COOR_c$, —$CONR_aR_c$; wherein $R_a$ and R are independently of each other H or (C1-6)alkyl and $R_c$ is —H, —(C1-6)alkyl, —NH—$(CH_2)_n$—$CO_2R_a$ or —NH—$(CH_2)_p$—$SO_3R_a$, wherein n, p is 1, 2, or 3 and $R_a$ is —H or —(C1-6)alkyl.

15. Method according to claim 14 wherein L is a straight-chain C(1-12)alkyl.

16. Method according to claim 14 wherein X is H, —$OR_a$, —$COOR_c$, —$CONR_aR_c$, wherein $R_a$ is H or (C1-6)alkyl and $R_c$ is —H, —(C1-6)alkyl, —NH—$CH_2$—$CO_2R_a$ or —NH—$(CH_2)_2$—$SO_{3p}R_a$, wherein $R_a$ is —H or —(C1-6)alkyl.

17. Method according to claim 14 wherein -L-X is —(C1-6)alkyl-$COOR_a$ wherein $R_a$ is —H or —(C1-6)alkyl.

18. Method according to claim 1, wherein the compound of formula V is administered in combination with at least one further therapeutically active agent.

19. Method according to claim 1, wherein the compound of formula V is in a form of a pharmaceutical composition comprising at least one pharmaceutically acceptable carrier.

\* \* \* \* \*